US012349908B1

(12) United States Patent
Fan et al.

(10) Patent No.: US 12,349,908 B1
(45) Date of Patent: Jul. 8, 2025

(54) SPRINGS FOR LOCKOUT ASSEMBLIES, AND ASSOCIATED SYSTEMS, DEVICES, AND METHODS

(71) Applicant: LEXINGTON MEDICAL, INC., Billerica, MA (US)

(72) Inventors: Max Fan, Boston, MA (US); Andrew Marecki, Wilbraham, MA (US); David T. Moy, Jr., Wellesley, MA (US)

(73) Assignee: Lexington Medical, Inc., Bedford, MA (US)

( * ) Notice: Subject to any disclaimer, the term of this patent is extended or adjusted under 35 U.S.C. 154(b) by 0 days.

(21) Appl. No.: 18/587,760

(22) Filed: Feb. 26, 2024

(51) Int. Cl.
*A61B 17/072* (2006.01)
*A61B 17/29* (2006.01)
(52) U.S. Cl.
CPC ............... *A61B 17/07207* (2013.01); *A61B 2017/2946* (2013.01)
(58) Field of Classification Search
CPC ................................................ A61B 17/07207
See application file for complete search history.

(56) References Cited

U.S. PATENT DOCUMENTS

| | | | |
|---|---|---|---|
| 10,433,842 B2 | 10/2019 | Amariglio et al. | |
| 10,856,871 B2 | 12/2020 | Somekh et al. | |
| 11,116,501 B1 | 9/2021 | Marecki | |
| 11,166,723 B2 | 11/2021 | Somekh et al. | |
| 11,376,003 B2 | 7/2022 | Somekh et al. | |
| 11,622,764 B2 | 4/2023 | Marecki et al. | |
| 2010/0094091 A1* | 4/2010 | Cappola | A61B 17/072 600/137 |
| 2022/0183688 A1 | 6/2022 | Moy, Jr. et al. | |
| 2022/0387025 A1 | 12/2022 | Marecki et al. | |
| 2023/0255626 A1 | 8/2023 | Marecki et al. | |

* cited by examiner

*Primary Examiner* — Nathaniel C Chukwurah
(74) *Attorney, Agent, or Firm* — Perkins Coie LLP

(57) ABSTRACT

Springs for lockout assemblies, such as for single-use lockout assemblies implemented in reloadable cartridge assemblies of surgical staplers, and associated systems, devices, and methods are disclosed herein. In one embodiment, a spring includes (a) a hook portion at a first end portion of the spring opposite the second end of the spring, and (b) a loop portion. In an absence of external force applied to the spring, the loop portion can be generally positioned at a first side of the hook portion opposite the second end portion of the spring such that the hook portion is positioned generally along a plane positioned between the loop portion and the second end portion. In some embodiments, the spring is a leaf spring, includes a cutout extending at least partway between the hook portion and the second end portion, and/or includes a notch at the second end portion.

20 Claims, 15 Drawing Sheets

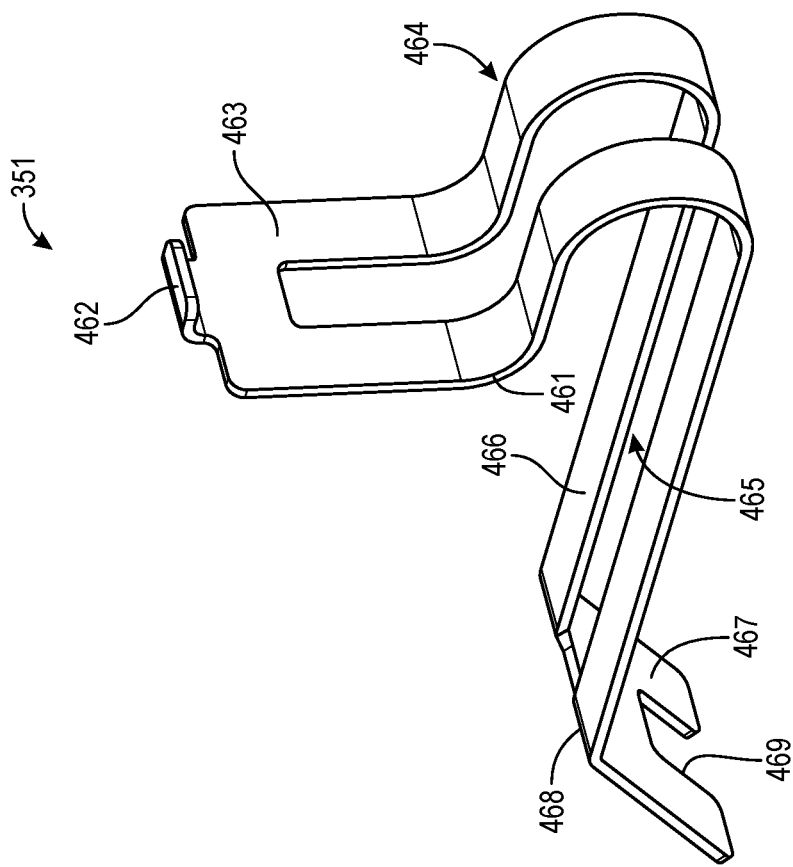
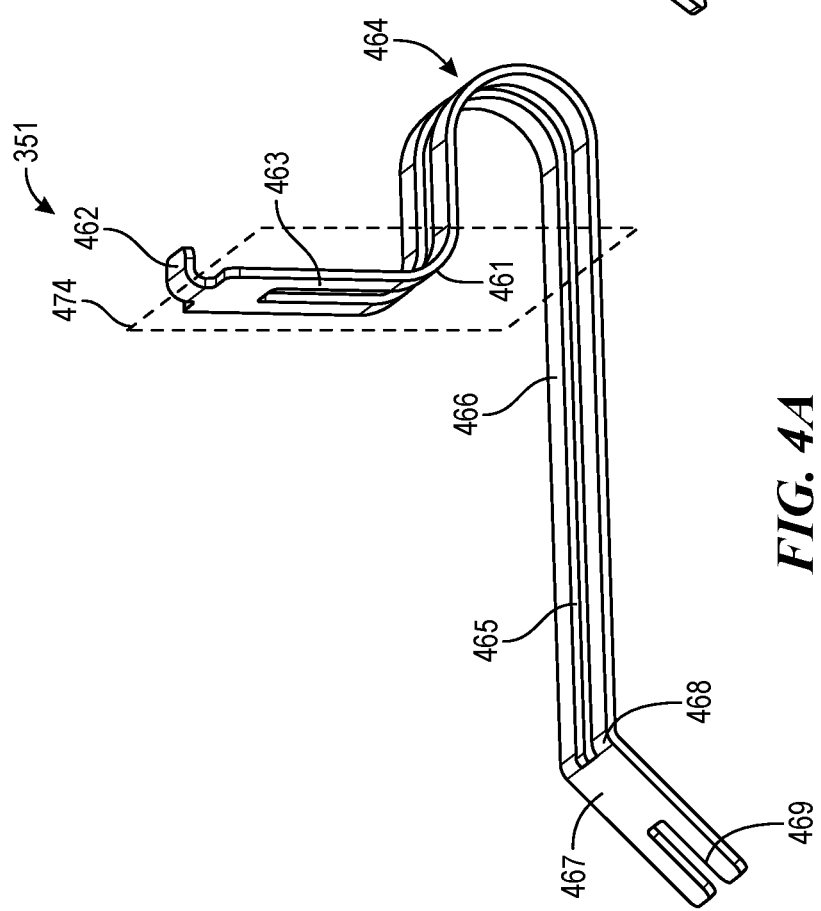
FIG. 4B
FIG. 4A

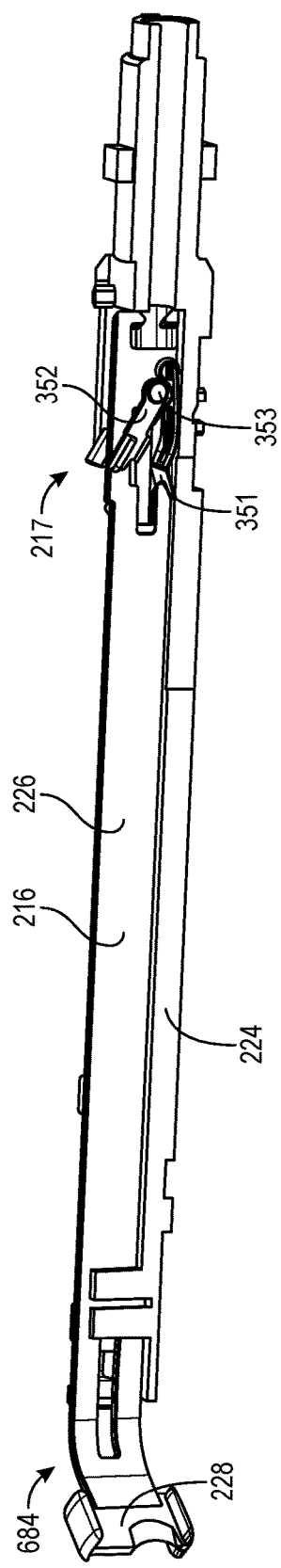
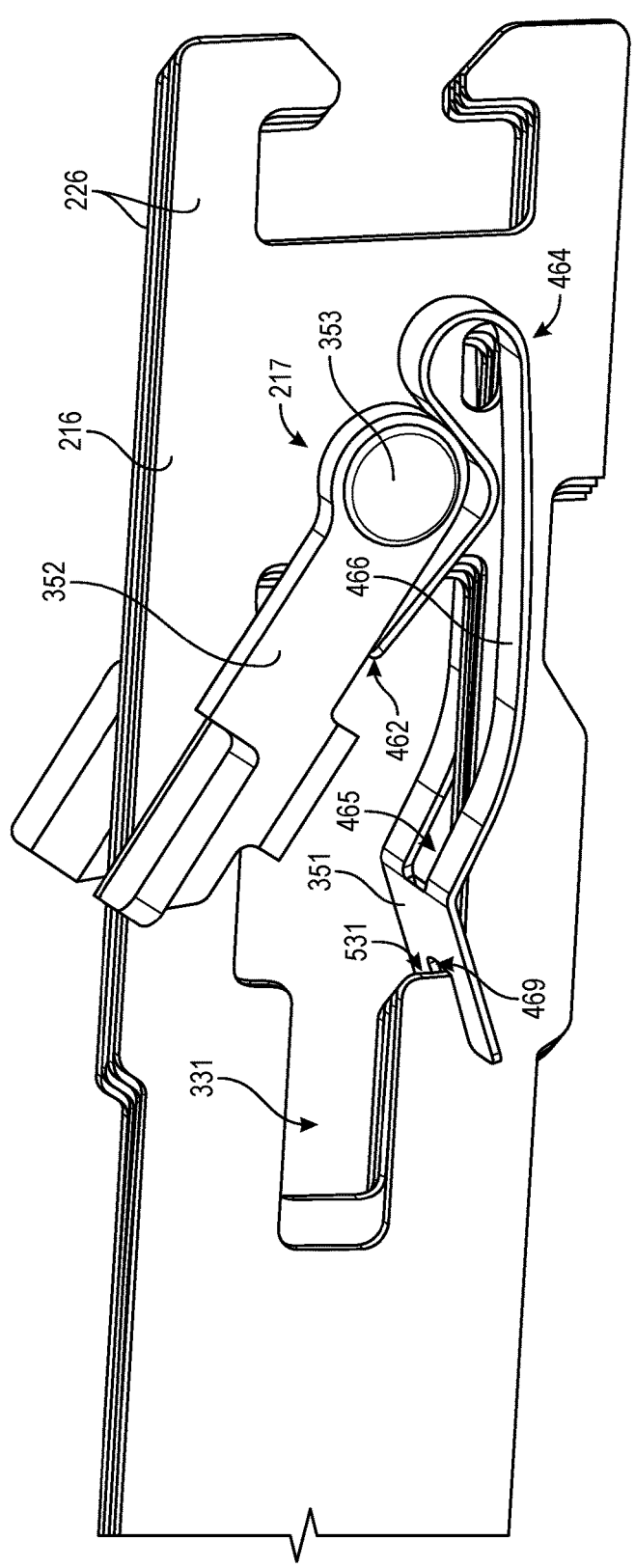
FIG. 6A
FIG. 6B

SPRINGS FOR LOCKOUT ASSEMBLIES, AND ASSOCIATED SYSTEMS, DEVICES, AND METHODS

TECHNICAL FIELD

The present disclosure relates generally to surgical devices. For example, several embodiments of the present technology relate to springs for lockout assemblies, such as single-use lockout assemblies implemented in reloadable cartridge assemblies of surgical staplers, and to associated systems, devices, and methods.

BACKGROUND

A surgical handle assembly and/or a surgical reloadable cartridge assembly can be used in a number of surgical devices. One example includes use in—or as part of—a surgical stapler. A surgical stapler is a fastening device used to clamp tissue between opposing jaw structures to join tissue using surgical fasteners. Surgical staplers can include two elongated members used to clamp the tissue. One of the elongated members can include one or more staple cartridges, and the other elongated member can include an anvil that can be used to form a staple when driven from the staple cartridge. Some surgical staplers are equipped with an electric motor that can provide the power to clamp tissue, deliver staples, and provide power for other aspects of a surgical stapler.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments shown, but are provided for explanation and understanding.

FIGS. 4A and 4B are partially schematic side perspective views of a spring configured in accordance with various embodiments of the present technology.

FIGS. 6A and 6B are partially schematic side perspective views of a lockout assembly on an articulated blade assembly, in accordance with various embodiments of the present technology.

DETAILED DESCRIPTION

Figure 1:
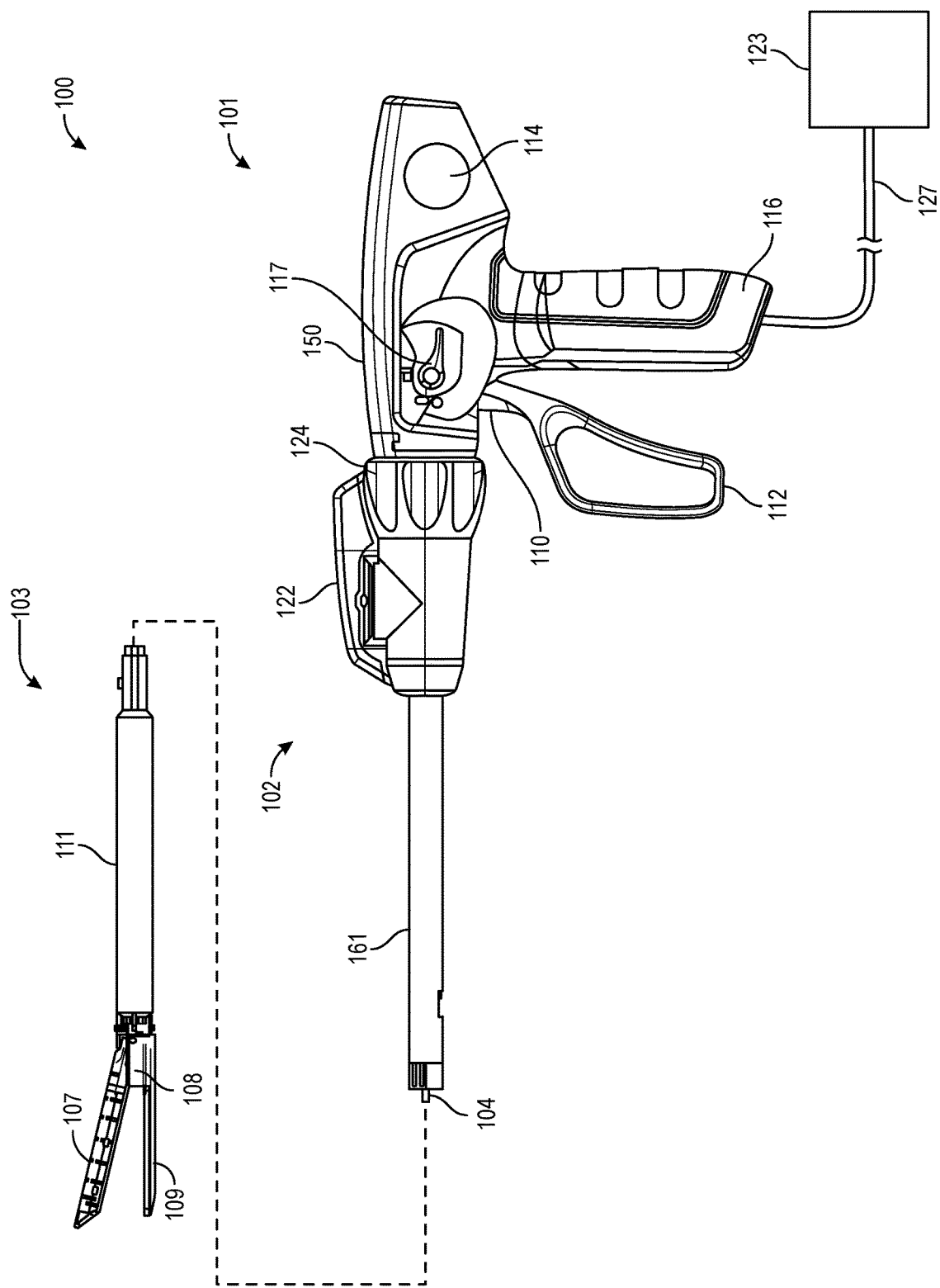
FIG. 1 is a partially schematic diagram of a surgical stapling system configured in accordance with various embodiments of the present technology.

The present disclosure is generally directed to springs for lockout assemblies and associated systems, devices, and methods. Specific details of several embodiments of the present technology are described herein with reference to FIGS. 1-10B. Although many of the embodiments are described below with reference to springs for single-use lockout assemblies implemented in reloadable cartridge assemblies of surgical staplers, other applications and other embodiments in addition to those described herein are within the scope of the present technology. For example, unless otherwise specified or made clear from context, the springs can be used in other assemblies besides single-use lockout assemblies, in other components of surgical staplers besides reloadable cartridge assemblies, in other medical and/or surgical instruments besides surgical staplers, and/or in non-medical instruments or devices. Furthermore, although many of the embodiments are described below with reference to springs for single-use lockout assemblies implemented in reloadable cartridge assemblies that are usable with powered devices (e.g., powered handle assemblies, powered surgical stapler handle assemblies, powered surgical staplers), the springs, single-use lockout assemblies, and/or reloadable cartridge assemblies can be useable with manual devices (e.g., manual handle assemblies, manual surgical stapler handle assemblies, manual surgical staplers).

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the term "physician" shall be understood to include any type of medical personnel who may be performing or assisting a medical procedure and, thus, is inclusive of a doctor, a nurse, a clinician, a medical technician, other similar personnel, and any combination thereof. As used herein, the term "patient" and "subject" should be considered to include human and/or non-human (e.g., animal) patients upon which a medical procedure is being performed.

As used herein, the terms "vertical," "lateral," "horizontal," "up," "upward," "upper," "lower," "down," "downward," "top," "bottom," and the like can refer to relative directions or positions of features illustrated in a drawing in view of the orientation or perspective shown in that drawing. For example, "bottom" can refer to a feature positioned closer to the bottom of a page/illustrated perspective than another feature. These terms, however, should be construed broadly to correspond to other orientations, such as inverted or inclined orientations where top/bottom, over/under, above/below, up/down, and left/right can be interchanged depending on the perspective.

A. Overview

A surgical stapler can include a surgical handle assembly and a reloadable cartridge assembly. The reloadable cartridge assembly can be releasably attached to the surgical handle assembly. Thereafter, a user can actuate a movable handle of the surgical handle assembly to clamp a first elongated member and a second elongated member of the reloadable cartridge assembly together (e.g., to grip tissue). Once the first elongated member and the second elongated member are clamped together, a user can engage a power trigger to actuate an electric motor of the surgical handle assembly and a corresponding drivetrain to move a blade assembly in the reloadable cartridge assembly along a stroke of the blade assembly (e.g., to cut and/or staple tissue clamped between the first elongated member and the second elongated member).

A reloadable cartridge assembly can include a single-use lockout assembly that can be triggered or engaged whenever the blade assembly is advanced distally along its stroke by a threshold amount. When the lockout assembly is triggered or engaged, a lockout mechanism of the lockout assembly can pose an obstacle (referred to herein as a "lockout obstacle") to subsequent distal advancement of the blade assembly beyond a point along the stroke of the blade assembly. Such a lockout assembly is used to ensure a single use of the reloadable cartridge assembly (at least until it has been reloaded). Stated another way, once the blade assembly of the reloadable cartridge assembly has been advanced distally along its stroke by the threshold amount, the lockout assembly can be triggered to prevent subsequent reuse or refiring of the reloadable cartridge assembly to avoid/prevent accidentally cutting tissue without stapling the tissue.

Many single-use lockout assemblies employ a wire spring to bias the lockout mechanism in a desired direction such that, when a blade assembly is advanced distally along its stroke by the threshold amount, a lockout mechanism is deployed using the wire spring to prevent subsequent reuse or refiring of the reloadable cartridge assembly. Such wire springs, however, typically require tools for proper installation, are relatively easily deformed, have a relatively low preload, and/or are often installed incorrectly.

To address the above concerns, several embodiments of the present technology are directed to improved springs (e.g., leaf springs) for use in lockout assemblies in lieu of the wire springs discussed above. Springs configured in accordance with the present technology can be installed without tools, and have a relatively greater elasticity, resistance to permanent deformation, and relatively higher preload as compared with conventional springs. The springs of the present technology also have shapes and other features that facilitate visual inspection of the spring to verify proper installation. In addition, several of the springs described herein include self-centering features to increase the probability that a corresponding lockout assembly is properly triggered/deployed even when a corresponding blade assembly is articulated away from its straight or resting position. Furthermore, several of the springs described herein include self-correcting features that facilitate moving the spring from an incorrectly installed state to a correctly installed state. Therefore, springs of the present technology are expected to decrease the risk that corresponding lockout assemblies are improperly triggered/deployed when a corresponding blade assembly is advanced distally along its stroke by the threshold amount. In other words, springs of the present technology are expected to decrease the risk of reusing or refiring a reloadable cartridge assembly and, accordingly, mitigate or eliminate the chances of accidentally cutting tissue without stapling the tissue.

B. Selected Embodiments of Springs for Single-Use Lockout Assemblies, and Associated Systems, Devices, and Methods FIG. 1 is a partially schematic diagram of a surgical stapling system 100 ("the system 100") configured in accordance with various embodiments of the present technology. As shown, the system 100 can include a surgical stapling apparatus 101 ("the surgical stapler 101") having a surgical handle assembly 102 and/or a surgical reloadable cartridge assembly 103 (e.g., a disposable loading unit). The surgical reloadable cartridge assembly 103 can be releasably secured to a distal end of an elongated body 161 of the surgical handle assembly 102, such as to a drive shaft 104 of the surgical handle assembly 102.

In the illustrated embodiment, the reloadable cartridge assembly 103 includes a shaft 111, a first elongated member 107, and a second elongated member 109. The first elongated member 107 and the second elongated member 109 can be used to clamp tissue, and are also referred to herein as "jaws." One of the elongated members (e.g., the first elongated member 107) can house one or more staple cartridges. The other elongated member (e.g., the second elongated member 109) can include an anvil that can be used to form a staple when driven from the staple cartridge (e.g., by a blade assembly (not shown in FIG. 1), as discussed in greater detail below). In some embodiments, the reloadable cartridge assembly 103 can further include a stabilizing bracket 108 that can help to hold the first elongated member 107 and the second elongated member 109 in alignment with one another and/or that can function as a tissue shield to prevent or hinder tissue from being clamped between the first elongated member 107 and the second elongated member 109 at a location more proximal than a distal end portion of the stabilizing bracket 108. In these and other embodiments, the reloadable cartridge assembly 103 can include one or more rows of staples having a linear length. For example, a row of staples can have a linear length between, e.g., approximately 30 mm and approximately 60 mm. In a number of embodiments, third party reloadable cartridges and/or reloadable cartridge assemblies may be used with the surgical handle assembly 102 and embodiments of the surgical handle assembly 102 may be configured to receive the same.

The surgical handle assembly 102 can include a radial positioner 124, an articulation assembly activated by an articulation knob 122, a non-movable handle 116 ("the stationary handle 116"), and a movable handle 112. When the reloadable cartridge assembly 103 is releasably secured to the distal end of the elongated body 161 of the surgical handle assembly 102, the reloadable cartridge assembly 103 can be actuated using the articulation knob 122 and/or the radial positioner 124 to reach a stapling site. For example, the radial positioner 124 can be used to rotate the reloadable cartridge assembly 103. Additionally, or alternatively, the articulation knob 122 can be used to position the first elongated member 107 and/or the second elongated member 109 at a particular angle for stapling. The articulation knob 122 can be rotationally actuatable, and the reloadable cartridge assembly 103 can rotate about an axis of a particular plane in response to the articulation knob 122 being rotationally actuated by a physician. The movable handle 112 can be used to clamp and unclamp the first elongated member 107 and the second elongated member 109 together (e.g., to clamp or grip tissue).

As shown, the surgical handle assembly 102 further includes a power trigger 110, a selector lever 117, and a manual retraction or bailout handle 150. The power trigger 110 can be used to activate an electric motor (not shown in FIG. 1) of the surgical handle assembly 102 to move a gear rack (not shown in FIG. 1) distally. The selector lever 117 can include a number of settings, which can include a locked position (e.g., a safety-activated position), an unlocked position (e.g., a fire position, a safety-deactivated position), and a reverse position. While the selector lever 117 is in the locked position, the movable handle 112 may be used to clamp and unclamp the first elongated member 107 and the second elongated member 109 together, but the power trigger 110 may be electrically deactivated or disabled such that actuation of the power trigger 110 does not activate the electric motor. When the selector lever 117 is in the unlocked position, the power trigger 110 may be enabled such that actuation of the power trigger 110 can supply power to the electric motor (e.g., to move the gear rack distally). When set to the reverse (e.g., retract) position, the selector lever 117 can cause the electric motor to be activated (e.g., to move the gear rack proximally). In some embodiments, the reverse position of the selector lever 117 can be a momentary position. Although not shown in the illustrated embodiment, the surgical handle assembly 102 can include a safety switch and a reverse button that are separate from one another (e.g., in addition to or in lieu of the selector lever 117) in other embodiments of the present technology.

In the illustrated embodiment, the surgical handle assembly 102 also includes a manual retraction or bailout handle 150. The bailout handle 150 can be used, for example, in the event the surgical stapler 101 or another component of the system 100 malfunctions, such as to manually open or separate the first elongated member 107 and the second elongated member 109 away from one another such that they no longer clamp tissue.

In some embodiments, the surgical handle assembly 102 can include a user feedback mechanism 114 that is usable to audibly or visually alert or inform a physician of one or more statuses of the system 100 (e.g., of the surgical handle assembly 102 and/or the surgical stapler 101). In the illustrated embodiment, the user feedback mechanism 114 includes a visible indicator, such as a LED. In some embodiments, the user feedback mechanism 114 can, for example, emit various colors to inform a physician of various states of the system 100. As a specific example, the user feedback mechanism 114 can emit a steady (e.g., non-flashing) green color to inform a physician when everything is fine; a flashing green color when the surgical handle assembly 102 is in the ready to fire position; a yellow color when a possible obstruction is detected, when the electric motor has stalled, and/or when the drivetrain is stopped for an obstruction, such as at an end of a firing stroke or upon encountering an actuated single use lockout mechanism; and/or a red color when a major system error or safety issue is detected. In some embodiments, the user feedback mechanism 114 can additionally, or alternatively, emit one or more sounds (e.g., beeps) that can, for example, change in pitch or frequency to inform a physician of certain events or statuses. Although illustrated on a side of the surgical handle assembly 102, the user feedback mechanism 114 can be positioned at other locations on the surgical handle assembly 102 in other embodiments of the present technology, such as on a top or bottom of the surgical handle assembly 102.

Although not shown in FIG. 1, the surgical handle assembly 102 can include a power source, such as a battery. The power source (e.g., battery) can be rechargeable (e.g., via an AC power supply) or disposable. If a rechargeable battery is used, the battery can be positioned so that it can be either removed or recharged. If a disposable battery is used, the stationary handle 116 can include a drain so that the battery can be drained prior to disposal.

In these and other embodiments, the surgical handle assembly 102 can include or be (e.g., releasably) coupled to a power cord 127. For example, the power cord 127 can be used to electrically couple the surgical handle assembly 102 (e.g., a battery and/or an electric motor of the surgical handle assembly 102) to a power source 123 positioned external to the surgical handle assembly 102. In turn, the power source 123 can supply AC or DC current to the surgical handle assembly 102 to power various components of the surgical handle assembly 102. If AC power is used, a power converter can be used to convert 120V or 240V AC, at either 50 or 60 Hz, to 24V, or any other suitable voltage, DC.

Additional details regarding surgical staplers and surgical handle assemblies are provided in U.S. patent application Ser. No. 17/833,302 and U.S. patent application Ser. No. 18/391,251, the disclosures of which are both incorporated by reference herein in their entireties. Furthermore, although the surgical reloadable cartridge assembly 103 is described above in relation to a powered surgical handle assembly, the reloadable cartridge assembly 103 can be used with manual surgical handle assemblies, such as manual surgical stapler handle assemblies. Additional details regarding examples of such manual surgical handle assemblies are provided in U.S. patent application Ser. No. 15/481,949, U.S. patent application Ser. No. 16/027,579, U.S. patent application Ser. No. 16/577,097, U.S. patent application Ser. No. 16/249,520, U.S. patent application Ser. No. 17/686,730, U.S. patent application Ser. No. 16/845,217, and U.S. patent application Ser. No. 17/241,538, which are incorporated by reference herein in their entireties.

Figure 2:
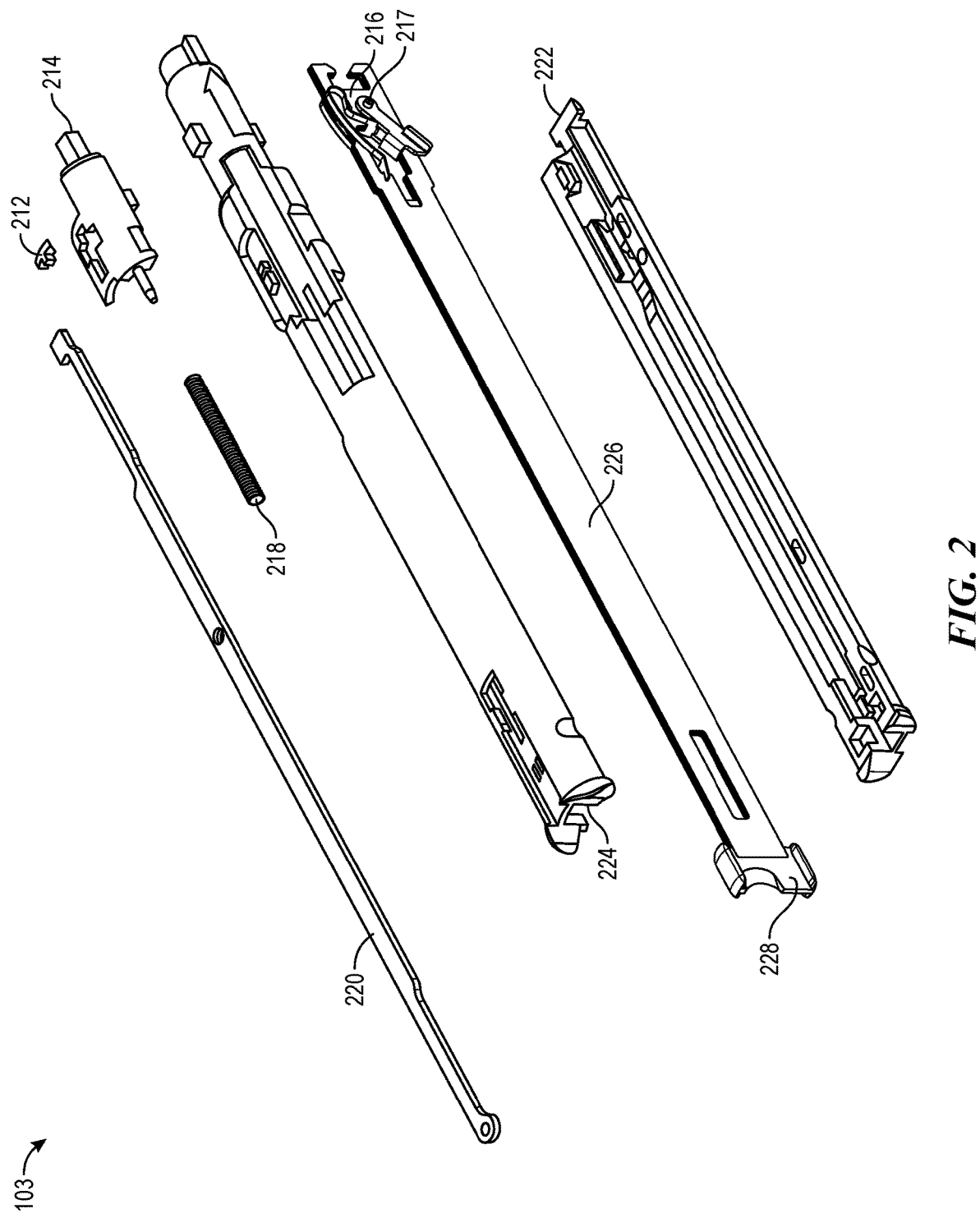
FIG. 2 is a partially schematic exploded view of a portion of a surgical reloadable cartridge assembly configured in accordance with various embodiments of the present technology.

FIG. 2 is a partially schematic exploded view of a portion of the surgical reloadable cartridge assembly 103 of FIG. 1. As shown, the surgical reloadable cartridge assembly 103 can include a blade lock 212, a lock slider 214, a spring 218, an articulation arm 220, a first cover portion 222, a second cover portion 224, a blade assembly 216, and a lockout assembly 217 (e.g., a single-use lockout assembly). The blade assembly 216 can include a number of leaves 226 and an I-beam 228.

The lock slider 214 is configured to engage the blade lock 212 and actuate the blade lock 212 radially from a first position to a second position. The spring 218 can be configured to bias the lock slider 214 in a proximal direction such that the lock slider 214 is engaged with the blade lock 212 and the blade lock 212 is in the first position. The first position, for example, can be a secure position that locks the blade assembly 216. The blade assembly 216 can be locked when the blade lock 212 is between the blade assembly 216 and the lock slider 214. The lock slider 214 can be configured to move proximally to engage the blade lock 212 and actuate the blade lock 212 from the second position to the first position. The blade lock 212 can actuate radially to the second position in response to the lock slider 214 moving in a distal direction when the reloadable cartridge assembly 103 is coupled to a surgical handle assembly (e.g., the surgical handle assembly 102 of FIG. 1). For example, the blade assembly 216 can be unlocked when the lock slider 214 is between the blade assembly 216 and the blade lock 212.

Figure 3:
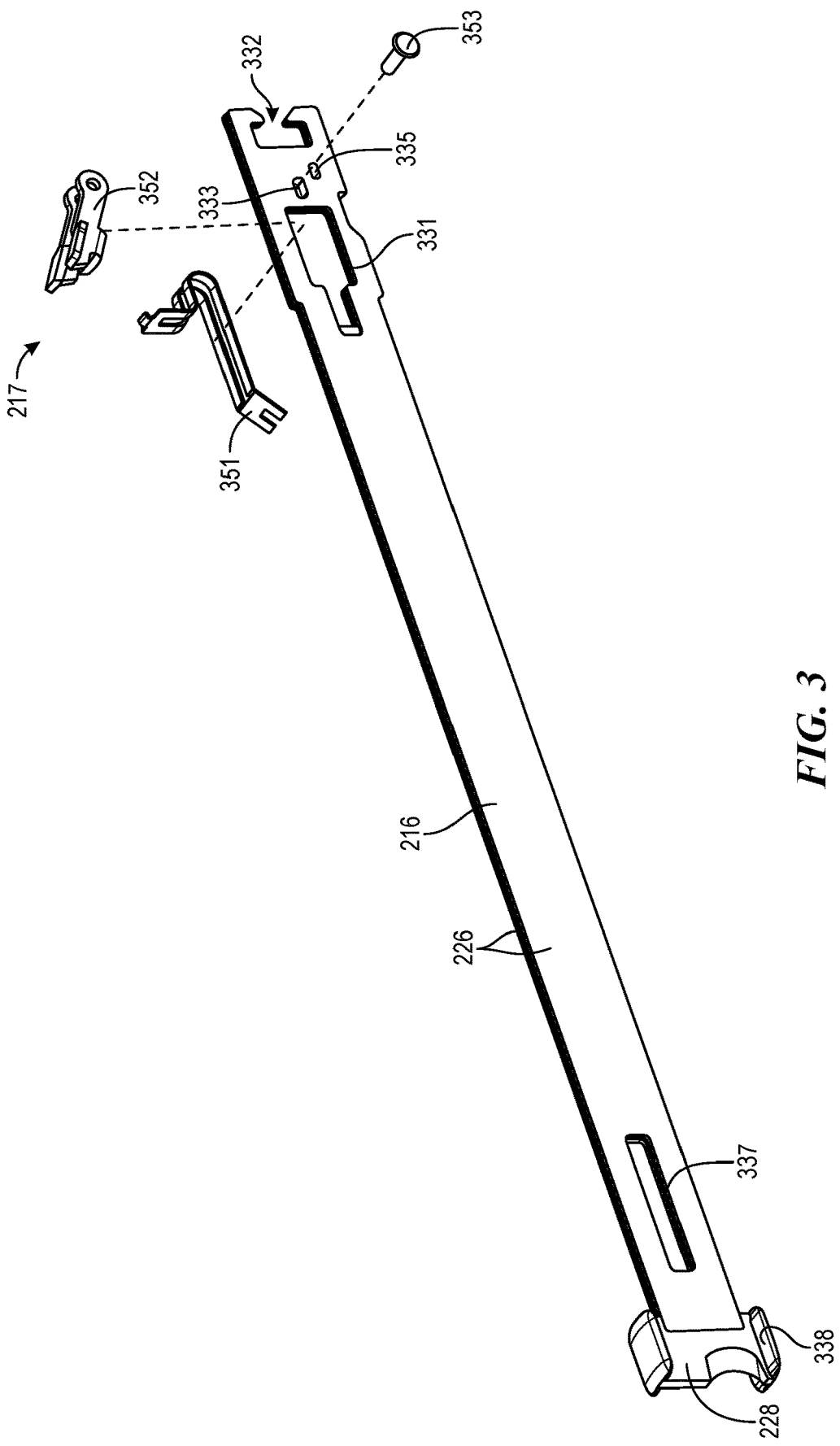
FIG. 3 is a partially schematic exploded view of a lockout assembly about a blade assembly and configured in accordance with various embodiments of the present technology.

FIG. 3 is a partially schematic exploded view of the lockout assembly 217 and the blade assembly 216 of FIG. 2, rotated roughly 180 degrees about a longitudinal axis of the blade assembly 216 relative to the orientations of the lockout assembly 217 and the blade assembly 216 shown in FIG. 2. As shown in FIG. 3, the lockout assembly 217 includes a mechanical latch 352 (or lever), a pin 353 (or rivet), and a spring 351. As also shown in FIG. 3, the leaves 226 of the blade assembly 216 include a number of openings. For example, the leaves 226 can each include a first opening 331; a second opening 333; and a third opening 335. The first openings 331 and the second openings 333 in the leaves 226 are configured to accommodate the lockout assembly 217. More specifically, as discussed in greater detail below, when the lockout assembly 217 is installed with the blade assembly 216 and is in an assembled state, the mechanical latch 352 is at least partially positioned within the first openings 331 and is pivotably held in place at one end using the pin 353 that extends through the second openings 333. Furthermore, the spring 351 can be installed in the first openings 331 in such a manner that it engages the mechanical latch 352 and biases an unpinned end of the mechanical latch 352 in a direction (e.g., a direction that extends toward a top of the leaves 226, such as toward a side of the leaves 226 opposite a bottom portion 338 of the I-beam 228). As discussed in greater detail below, the lockout assembly 217 can be used to prevent the reloadable cartridge assembly 103 from being fired more than one time.

Each of the leaves 226 of the blade assembly 216 can also include a fourth opening 337 (e.g., to increase or enhance flexibility of the leaves 226), and/or a slot 332. In some embodiments, the fourth openings 337 and/or the third opening 335 can be omitted. The slots 332 in the leaves 226 can be used to connect the blade assembly 216 to a drive shaft (e.g., the drive shaft 104 of FIG. 1) of a surgical handle assembly (e.g., the surgical handle assembly 102 of FIG. 1). When connected to a drive shaft, the blade assembly 216 can be moved distally or proximally as the drive shaft is moved distally or proximally.

FIGS. 4A and 4B are partially schematic side perspective views of the spring 351 of the lockout assembly 217 of FIGS. 2 and 3. As shown, the spring 351 is generally 'S' shaped and includes a first body portion 463, a second body portion 464 (sometimes also referred to herein as a "looped body portion," a "loop portion," and/or a "first bend"), a third body portion 466, and a fourth body portion 467 (sometimes also referred to herein as a "slanted portion"). The spring 351 further includes a hook portion 462 connected to the first body portion 463 at a first end portion of the spring 351, and a notch 469 formed in the fourth body portion 467 at a second end portion of the spring 351 opposite the first end portion. An end of the first body portion 463 opposite the hook portion 462 is connected to the second body portion 464 via a bend 461 (sometimes also referred to herein as a "second bend") in the spring 351. An end of the second body portion 464 opposite the bend 461 is connected to the third body portion 466, and an end of the third body portion 466 opposite the second body portion 464 is connected to the fourth body portion 467 via a bend 468 (sometimes also referred to herein as a "third bend") in the spring 351.

The second body portion 464 can be generally positioned at a side of the hook portion 462 and/or the first body portion 463 opposite at least a portion of the third body portion 466, the bend 468, the fourth body portion 467, and/or a notch 469 at the second end portion of the spring 351. For example, the hook portion 462 and/or the first body portion 463 can be positioned generally along a plane 474 (FIG. 4A) that is positioned between (a) the second body portion 464 and (b) at least the portion of the third body portion 466, the bend 468, the fourth body portion 467, and/or the notch 469. In some embodiments, the plane 474 can be generally parallel to and/or defined at least in part by a portion of the first body portion 463 that extends in the general vertical direction shown in FIGS. 4A and 4B.

The hook portion 462 includes a bend that, in the absence of external force applied to the spring 351, extends in a direction generally opposite to the direction of a bend of the second body portion 464. For example, in the absence of external force applied to the spring 351, at least part of the bend of the second body portion 464 can generally be a reflection of the bend of the hook portion 462 taken along a vertical line (not shown) positioned between the hook portion 462 and the second body portion 464 in FIG. 4A. Additionally, or alternatively, in the absence of external force applied to the spring 351, the bend of the hook portion 462 can be concave in a direction generally toward the second body portion 464 (e.g., in a direction generally away from the second end portion of the spring 351 and/or one or more components of the spring 351 positioned to the left of the plane 474 in FIG. 4A), and/or the bend of the second body portion 464 can be concave in a direction generally toward the hook portion 462, the first body portion 463, the bend 461, the third body portion 466, the bend 468, the fourth body portion 467, the notch 469, and/or the plane 474.

In these and other embodiments, at least in the absence of external force applied to the spring 351, the first body portion 463 can be oriented in a first orientation (e.g., the generally vertical orientation shown in FIGS. 4A and 4B, an orientation at least generally parallel to the plane 474). The third body portion 466 can be oriented in a second orientation (e.g., the generally horizontal orientation shown in FIGS. 4A and 4B, an orientation generally perpendicular to the plane 474) that is generally perpendicular (or at least generally skew perpendicular) to the first orientation. Additionally, or alternatively, at least in the absence of external force applied to the spring 351, the bend 468 can slant the fourth body portion 467 (*a*) in a direction generally downward with respect to the third body portion 466 and/or (b) in a direction generally downward and/or away from the hook portion 462 and/or the first body portion 463 of the spring 351, starting from the bend 468.

In these and still other embodiments, the bend 461 can be generally similar to the bend in the hook portion 462, but can generally be a reflection of the bend in the hook portion 462 taken across a horizontal line (not shown) positioned between the hook portion 462 and the bend 461 in FIG. 4A. For example, the bend 461 can be concave in a direction generally toward the second body portion 464 (e.g., in a direction generally away from the second end portion of the spring 351 and/or one or more components of the spring 351 positioned to the left of the plane 474 in FIG. 4A).

As shown in FIGS. 4A and 4B, the spring 351 further includes a cutout 465. The cutout 465 can extend at least partway between the hook portion 462 and the bend 468. For example, in the illustrated embodiment, the cutout 465 extends along at least part of the first body portion 463, the second body portion 464, and the third body portion 466 of the spring 351. As a specific example, the cutout 465 can extend along an entire length of the second body portion 464 and/or an entire length of the third body portion 466. Furthermore, in the illustrated embodiment, the spring 351 is a leaf spring. The spring 351 can be another suitable type of spring, however, in other embodiments of the present technology.

In some embodiments, the spring 351 can be formed of stainless steel, steel, nickel titanium alloy, or another suitable (e.g., biocompatible) material. For example, the spring 351 can be formed of a spring tempered stainless steel. As a specific example, the spring 351 can be formed of stainless steel that is cold worked (e.g., in a hardened state) to a higher tensile strength and/or to increase its upper limit of elasticity. As another specific example, the spring 351 can be formed of stainless steel that is heat treated to a higher tensile strength and/or to increase its upper limit of elasticity. In comparison with wire springs commonly used in conventional lockout assemblies, the spring 351 includes a greater amount of material contributing to the elasticity of the spring 351. As such, it is expected that the spring 351 will have a greater preload (e.g., even when partially deformed), a greater elasticity, and/or a greater resistance to permanent/irreversible deformation in comparison to the wire springs commonly used in lockout assemblies.

Figure 5A:
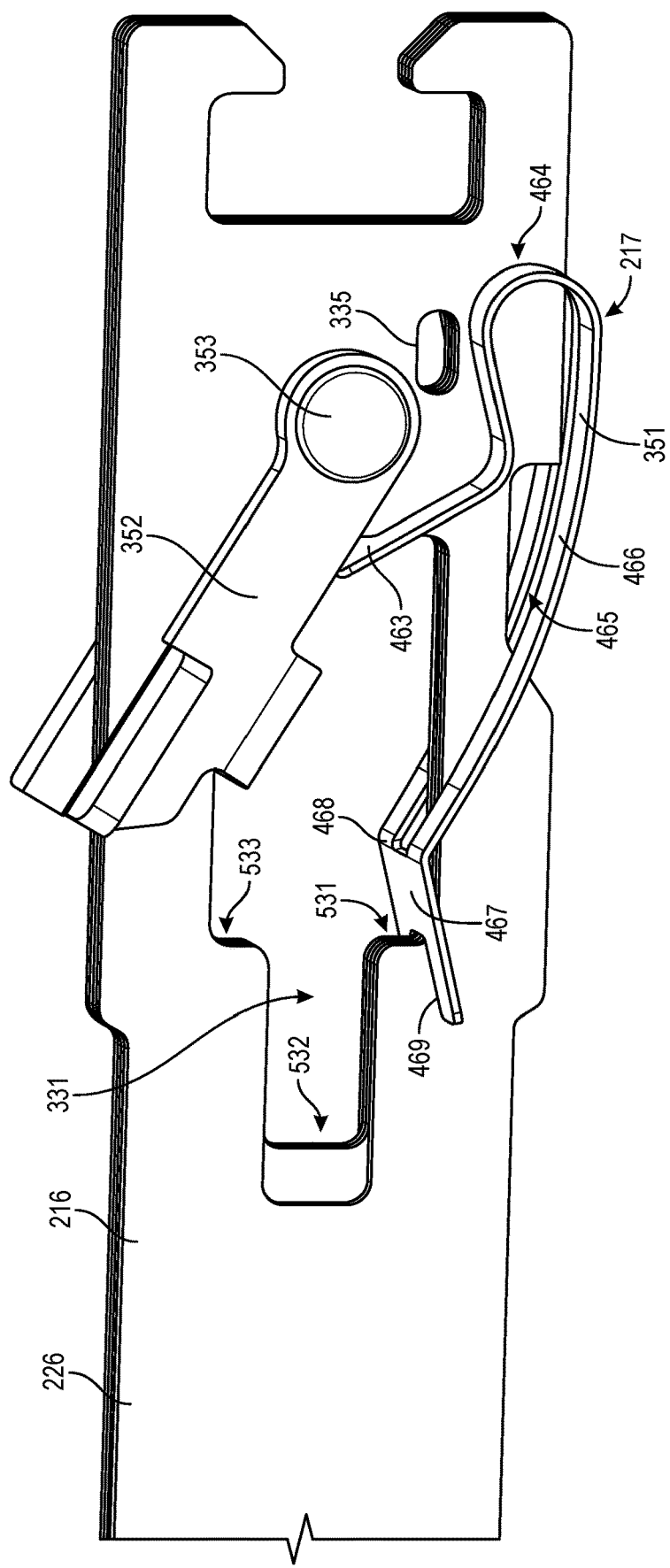
FIGS. 5A and 5B are a partially schematic side perspective view and a partially schematic, partially transparent side perspective view, respectively, of a lockout assembly installed with a blade assembly and configured in accordance with various embodiments of the present technology.
Figure 5B:
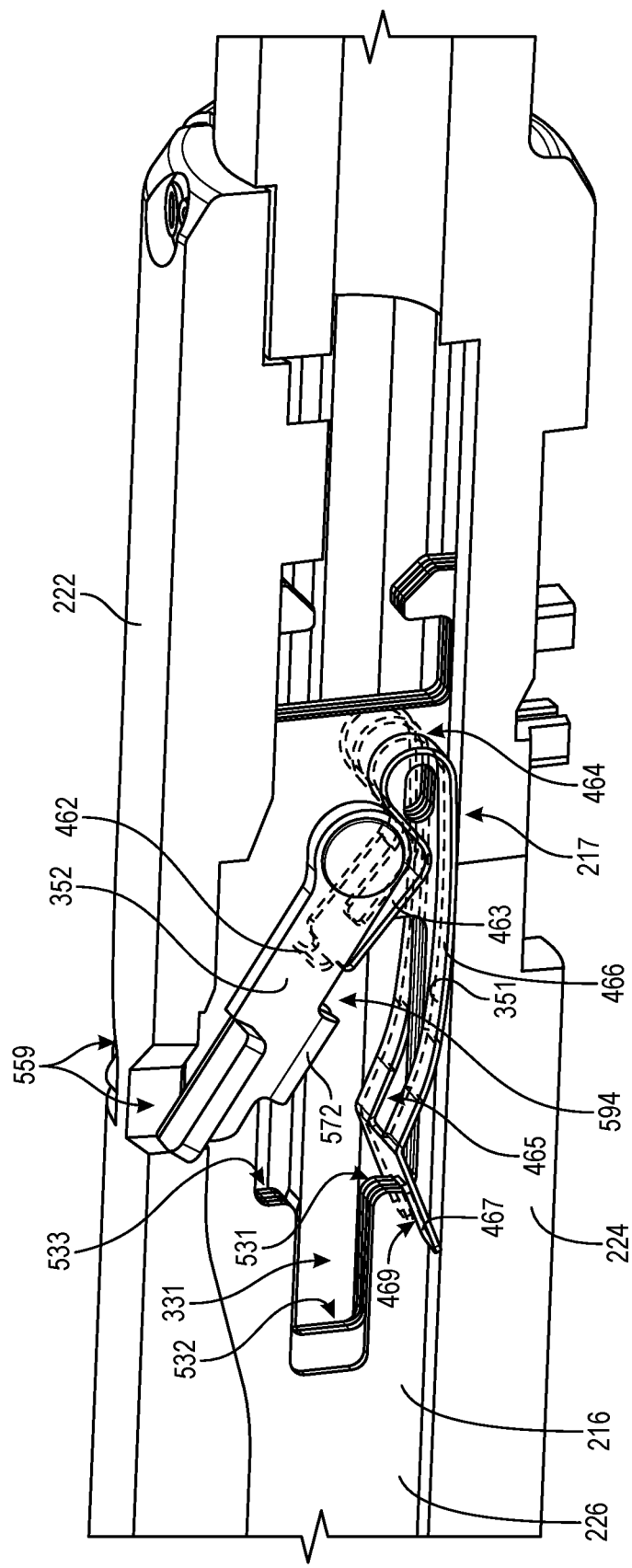

FIGS. 5A and 5B are a partially schematic side perspective view and a partially schematic, partially transparent side perspective view, respectively, of the lockout assembly 217 installed with the blade assembly 216. More specifically, FIG. 5A illustrates the lockout assembly 217 installed with the blade assembly 216 without the first cover portion 222 and the second cover portion 224 of FIG. 2 installed with the blade assembly 216, and FIG. 5B illustrates the lockout assembly 217 installed with the blade assembly 216 with the first cover portion 222 and the second cover portion 224 also installed with the blade assembly 216. In addition, FIG. 5C is a partially schematic, partial cross-sectional top view of the lockout assembly 217 installed with the blade assembly 216 with (a) the second cover portion 224 installed with the blade assembly 216 and (b) the first cover portion 222 and the top half of the blade assembly 216 removed/not shown.

Referring first to FIGS. 5A and 5B together, when the lockout assembly 217 is installed with the blade assembly 216, the mechanical latch 352 of the lockout assembly 217 can be at least partially positioned within the first openings 331 of the leaves 226 of the blade assembly 216, and can be pivotably held in place at one end via the pin 353 extending through the second openings 333 in the leaves 226. Furthermore, the spring 351 can be installed in the first openings 331 in such a manner that it engages the mechanical latch 352 and biases an unpinned end of the mechanical latch 352 in a generally upward direction in the perspective shown in FIGS. 5A and 5B. More specifically, the first openings 331 in the leaves 226 can include first edge portions 531 (sometimes also referred to herein as a "first lips"), second edge portions 532, and/or third edge portions 533 (sometimes also referred to herein as a "second lips"). When properly installed, the spring 351 can be positioned within the first openings 331 in the leaves 226 such that (a) the notch 469 formed in (or at) the end portion of the fourth body portion 467 of the spring 351 straddles and rests against the first edge portions 531; and (b) the leaves 226 of the blade assembly 216 are positioned within the cutout 465 in the spring 351 while at least part of the first body portion 463, the second body portion 464, and/or the third body portion 466 of the spring 351 straddle the leaves 226. Furthermore, as best shown in FIGS. 5B and 5C, when the spring 351 is properly installed, the hook portion 462 of the spring 351 (i) can be inserted in a notch positioned between a bridge portion 572 of the mechanical latch 352 and a center body portion 576 (FIG. 5C) of the mechanical latch 352, and (ii) can engage (or hook) the center body portion 576 of the mechanical latch 352.

The size, shape, and/or geometric features of the spring 351 can facilitate installing the spring 351 on the blade assembly 216 by hand (e.g., without tools). Additionally, or alternatively, the size, shape, and/or geometric features of the spring 351 can facilitate quickly verifying proper installation via visual inspection. This is unlike wire springs that are typically used for lockout assemblies as (i) those wire springs often require tweezers or other tools to position components of the wire springs at proper locations and (ii) proper installation of those wire springs is difficult to quickly verify via visual inspection given the size of components of the wire springs and the locations at which those wire springs engage the leaves of the blade assemblies and/or the mechanical latches of the lockout assemblies.

Figure 5C:
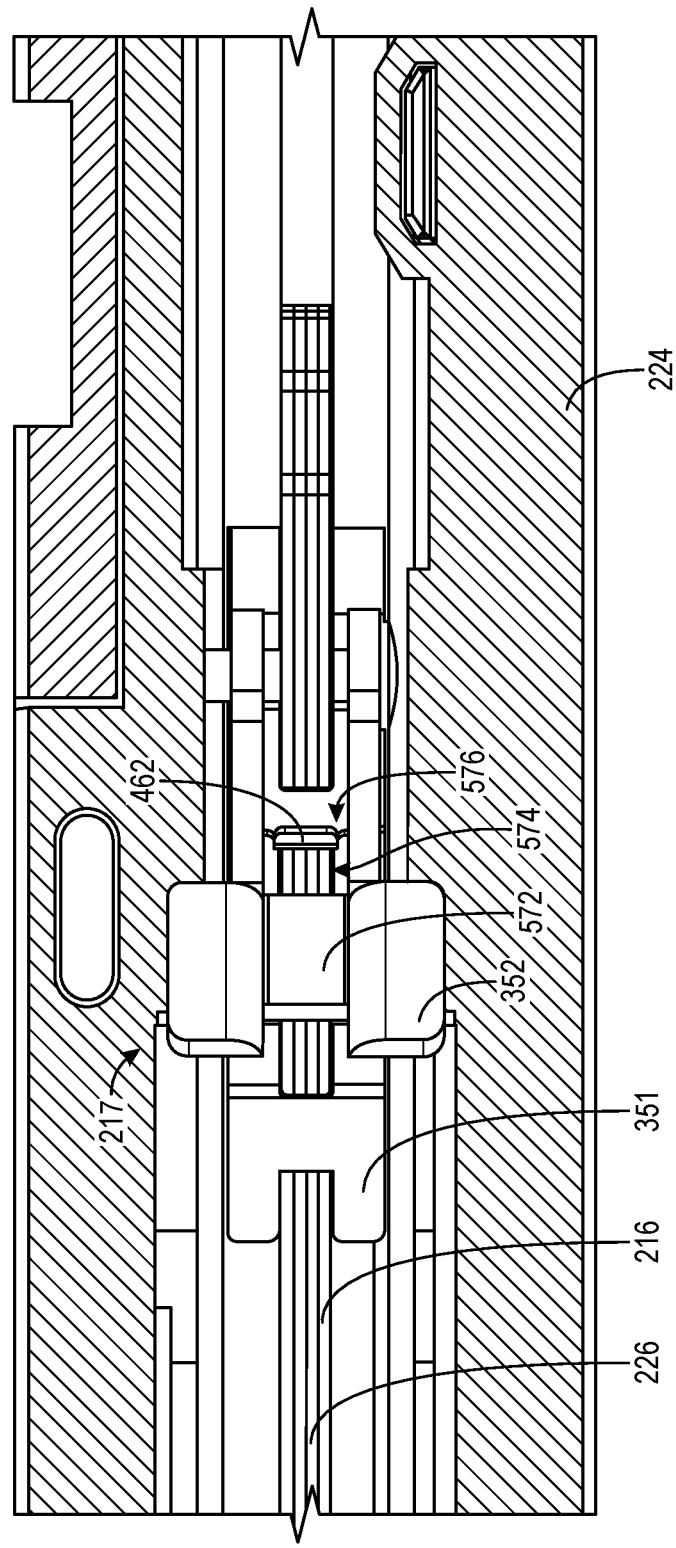
FIG. 5C is a partially schematic, partial cross-sectional top view of the lockout assembly and the blade assembly of FIGS. 5A and 5B.
Figure 5D:
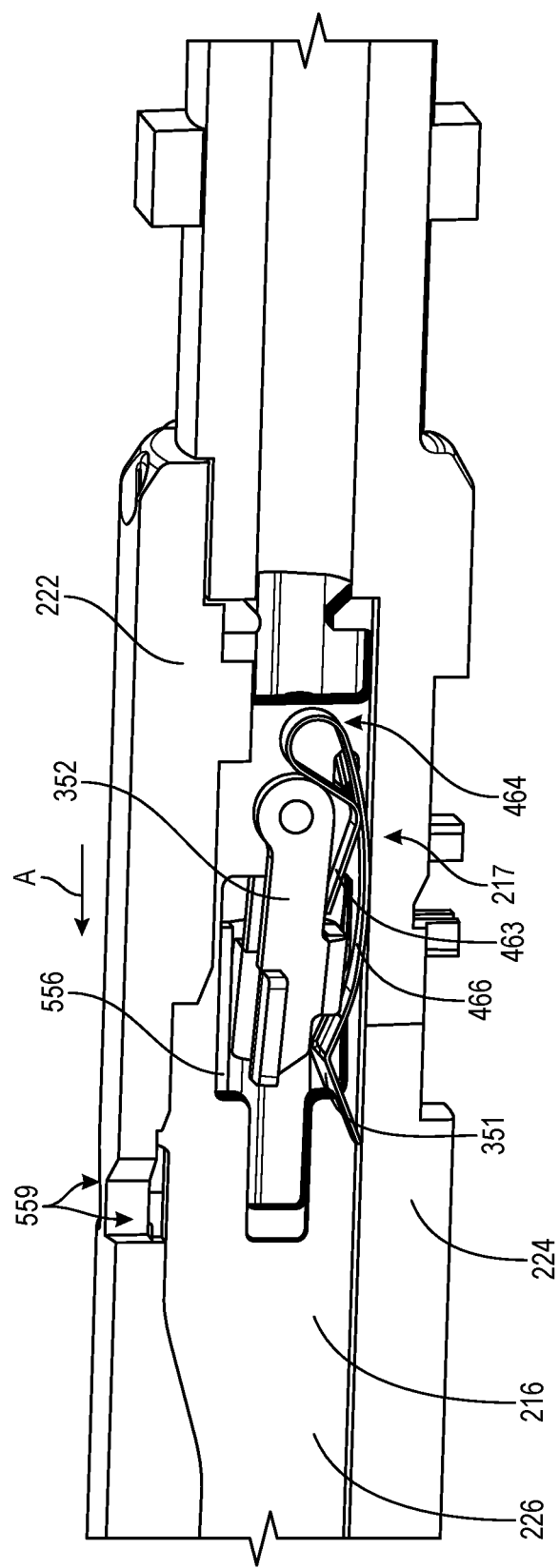
FIG. 5D is another partially schematic side perspective view of the lockout assembly and the blade assembly of FIGS. 5A-5C.

FIG. 5D is another partially schematic side perspective view of the lockout assembly 217 and the blade assembly 216 of FIGS. 5A-5C. More specifically, FIG. 5D illustrates the lockout assembly 217 installed with the blade assembly 216 and held in a first state (e.g., an undeployed, unlocked, untriggered, or loaded state) between the first cover portion 222 and the second cover portion 224. As shown, the first cover portion 222 includes a ledge 556 (e.g., a shelf, platform, lip, block) configured to engage the mechanical latch 352 and hold the lockout assembly 217 in the first state shown in FIG. 5D at least until the blade assembly 216 is distally advanced relative to the first cover portion 222 to a point at which the mechanical latch 352 clears a distal end/edge (not shown) of the ledge 556. Furthermore, when the second cover portion 224 is installed with the blade assembly 216, the second cover portion 224 can engage the second body portion 464, the third body portion 466, and/or the fourth body portion 467 of the spring 351 and apply a force against the spring 351 in a generally upward direction (e.g., in a direction generally toward the mechanical latch 352 and/or the first cover portion 222 shown in FIG. 5D). Thus, when the lockout assembly 217, the first cover portion 222, and the second cover portion 224 are installed with the blade assembly 216 and the mechanical latch 352 is positioned beneath the ledge 556 of the first cover portion 222, the second cover portion 224 can apply an generally upward force against the spring 351, thereby causing the spring 351 to bias the mechanical latch 352 in the generally upward direction while the ledge 556 prevents the unpinned end of the mechanical latch 352 from pivoting about the pin 353 in the generally upward direction. In other words, when the lockout assembly 217, the first cover portion 222, and the second cover portion 224 are installed with the blade assembly 216 and the mechanical latch 352 is positioned beneath the ledge 556 of the first cover portion 222, the spring 351 can be placed in a compressed state via the generally upwards force applied against the spring 351 by the second cover portion 224 and/or via a generally downwards force applied against the spring 351 by the ledge 556 of the first cover portion 222 via the mechanical latch 352. In the compressed state, at least a portion of the third body portion 466 and/or at least a portion of the second body portion 464 of the spring 351 can be positioned closer to the first body portion 463 of the spring 351 than they are when the spring 351 is in an uncompressed state.

When the lockout assembly 217 is in this first state, a corresponding reloadable cartridge assembly (e.g., the reloadable cartridge assembly 103 of FIG. 1) can be permitted to clamp and/or unclamp a first elongated member (e.g., the first elongated member 107 of FIG. 1) and a second elongated member (e.g., the second elongated member 109 of FIG. 1) without locking out the reloadable cartridge assembly. As used herein, the terms "locking out'" or "locked out" or "lockout" refer to a state in which the blade assembly 216 of a reloadable cartridge assembly is prevented from being advanced distally to or beyond a given point, such as a point at which the reloadable cartridge assembly is initially expected to begin cutting, stapling, or otherwise acting upon tissue clamped between the first elongated member and the second elongated member.

The lockout assembly 217 can be configured to transition between the first state shown in FIG. 5D and a second state (e.g., a deployed, locked, fired, triggered, released state) as shown in FIGS. 5A and 5B. More specifically, after the lockout assembly 217 is placed in the first state shown in FIG. 5D, the blade assembly 216 can be advanced distally relative to at least the first cover portion 222 (as shown by arrow A). As the blade assembly 216 is advanced distally by a threshold amount, the mechanical latch 352 can clear the distal end of the ledge 556 (FIG. 5D), and the spring 351 can transition from the compressed state (shown in FIG. 5D) toward an uncompressed state (shown in FIGS. 5A and 5B) and thereby move the lockout assembly 217 from the first state (shown in FIG. 5D) toward the second state (shown in FIGS. 5A and 5B). In particular, at the point where the mechanical latch 352 clears the distal end of the ledge 556, the ledge 556 no longer prevents rotation of the unpinned end of the mechanical latch 352, and the spring 351 is free to transition toward the uncompressed state. As the spring 351 transitions toward the uncompressed state, the spring 351 can pivot the unpinned end of the mechanical latch 352 in the generally upward direction toward the first cover portion 222 and transition the lockout assembly 217 to a third state (not shown) between the first state (shown in FIG. 5D) and the second state (shown in FIGS. 5A and 5B).

In some embodiments, a corresponding reloadable cartridge assembly can be designed such that the location at which the mechanical latch 352 clears the distal end of the ledge 556 corresponds to one or more other functions or features of the reloadable cartridge assembly. For example, the location can correspond to a point at or before which the blade assembly 216 or another component of the reloadable cartridge assembly is expected to initially engage with (e.g., contact, cut, staple) tissue clamped between a first elongated member and a second elongated member of the reloadable cartridge assembly. As a specific example, the location can correspond to a point at which the blade assembly 216 (e.g., the I-beam 228 of FIGS. 2 and 3) extends distally beyond a stabilizing bracket (e.g., the stabilizing bracket 108 of FIG. 1). In these and other embodiments, the location can correspond to a point at or before which the blade assembly 216 is used to initially expel staples from (e.g., the first and/or the second elongated member(s) of) the reloadable cartridge assembly.

As shown in FIGS. 5B and 5D, the first cover portion 222 can include one or more cavities 559 or cutouts on a side of the ledge 556 opposite the mechanical latch 352 shown in FIG. 5D. The one or more cavities 559 in the first cover portion 222 can be configured to capture the mechanical latch 352 (i) after the blade assembly 216 has been advanced distally by the threshold amount such that the mechanical latch 352 clears the distal end of the ledge 556 (FIG. 5D) and is pivoted in the generally upward direction toward the first cover portion 222 by the spring 351 and (ii) after the blade assembly 216 is subsequently retracted proximally beyond a given point to position or capture the mechanical latch 352 within the one or more cavities 559. When the mechanical latch 352 is fully captured in the one or more cavities 559, the lockout assembly 217 can be in the second state (e.g., the locked or lockout state) shown in FIGS. 5A and 5B. In the second state, the mechanical latch 352 of the lockout assembly 217 can present a lockout obstacle that prevents or hinders subsequent distal movement of the blade assembly 216 relative to the first cover portion 222 beyond a preset point. The present point can correspond to a location at which the mechanical latch 352 of the lockout assembly 217 abuts against a distal sidewall of the one or more cavities 559. As such, in the second state, the lockout assembly 217 can be used to prevent or hinder (e.g., accidental) reuse or refiring of the blade assembly 216.

In some embodiments, a corresponding reloadable cartridge assembly can be designed such that the location at which the mechanical latch 352 becomes fully captured in the one or more cavities 559 corresponds to one or more other functions or features of the reloadable cartridge assembly. For example, the location can correspond to a point that is positioned proximal to the location at which the mechanical latch 352 clears the distal end of the ledge 556 to transition the lockout assembly 217 from the first state to the third state. In other words, the location at which the mechanical latch 352 falls into the one or more cavities 559 can be positioned such that the lockout assembly 217 is moved to the second state when it is likely that the blade assembly 216 has already been used to cut tissue and/or expel staples (e.g., from the first and/or second elongated member(s)). Thus, the second state of the lockout assembly 217 is expected to prevent or hinder firing of the blade assembly 216 in situations in which (i) tissue clamped between the first elongated member and the second elongated member of a corresponding reloadable cartridge assembly is cut without being stapled (e.g., because staples have already or previously been expelled from at least a portion of the first and/or second elongated member(s)) and/or (ii) at least part of the tissue clamped between the first elongated member and the second elongated member may have already been cut and/or stapled such that at least the part of the tissue may not currently be adequately or securely held in place by the clamping force of the first elongated member and the second elongated member.

In some embodiments, the hook portion 462, the cutout 465, and/or the notch 469 of the spring 351 can assist with centering the spring 351 and/or the mechanical latch 352 about the leaves 226 of the blade assembly 216. For example, FIGS. 6A and 6B are partially schematic side perspective views of the lockout assembly 217 installed with the blade assembly 216 while at least a distal end portion 684 of the blade assembly 216 is articulated at an angle away from its straight or resting position (e.g., a position generally in line with a longitudinal axis of the blade assembly 216 in the absence of a force applied to the blade assembly 216). As best shown in FIG. 6B, the leaves 226 of the blade assembly 216 can be translated out of alignment with one another when the distal end portion 684 (FIG. 6A) of the blade assembly 216 is articulated in the manner shown in FIG. 6A. This can apply a force against the pin 353 of the lockout assembly 217, which (absent the hook portion 462, the cutout 465, and/or the notch 469 of the spring 351) could potentially cant or skew the mechanical latch 352 and/or the spring 351 to an extent such that the lockout assembly 217 malfunctions (e.g., the mechanical latch 352 is not captured in the one or more cavities 559 (FIGS. 5B and 5D) discussed above, and/or the mechanical latch 352 fails and does not prevent or hinder subsequent distal movement of the blade assembly 216 after the mechanical latch 352 has been captured in the one or more cavities 559).

Because the hook portion 462 (FIGS. 4A, 4B, 5B and 5C) of the spring 351 is (a) positioned within a notch between the bridge portion 572 (FIGS. 5B and 5C) and the center body portion 576 (FIG. 5C) of the mechanical latch 352 and (b) hooked on the center body portion 576 of the mechanical latch 352, the hook portion 462 of the spring 351 can limit the extent by which the mechanical latch 352 is permitted to cant or skew when the blade assembly 216 is articulated. Additionally, or alternatively, the cutout 465 and/or the notch 469 in the spring 351 can be slightly wider than the total thickness of the leaves 226 of the blade assembly 216 to allow the spring 351 some freedom of motion about the leaves 226 (e.g., as they translate out of alignment with one another when the blade assembly 216 is articulated). Such freedom of motion can assist with keeping the notch 469 in the spring 351 engaged with the first edge portions 531 of the first openings 331 in the leaves 226 and/or can assist with keeping the hook portion 462 engaged with the center body portion 576 of the mechanical latch 352, while limiting an extent by which the spring 351 can be canted or skewed relative to the leaves 226. In other words, the hook portion 462, the cutout 465, and/or the notch 469 of the spring 351 can assist (i) with keeping the spring 351 and/or the mechanical latch 352 centered about the leaves 226 and/or (ii) with limiting cant or skew of the spring 351 and/or the mechanical latch 352 relative to the leaves 226, even when the blade assembly 216 is articulated.

As discussed above with reference to FIGS. 5A and 5B, when the spring 351 is properly installed with the blade assembly 216, (a) the notch 469 formed in (or at) the end portion of the fourth body portion 467 of the spring 351 straddles and rests against the first edge portions 531 of the first openings 331 in the leaves 226; (b) the leaves 226 of the blade assembly 216 are positioned within the cutout 465 in the spring 351 while at least part of the first body portion 463, the second body portion 464, and/or the third body portion 466 of the spring 351 straddle the leaves 226; and (c) the hook portion 462 of the spring 351 is in a notch positioned between the bridge portion 572 of the mechanical latch 352 and a center body portion 576 (FIG. 5C) of the mechanical latch 352, and is engaged with the center body portion 576 of the mechanical latch 352. As also discussed above, the size, shape, and/or geometric features of the spring 351 make it relatively easy to verify proper installation of the spring 351 via visual inspection. Nevertheless, it is possible for the spring 351 to be improperly installed with the blade assembly 216.

Figure 7A:
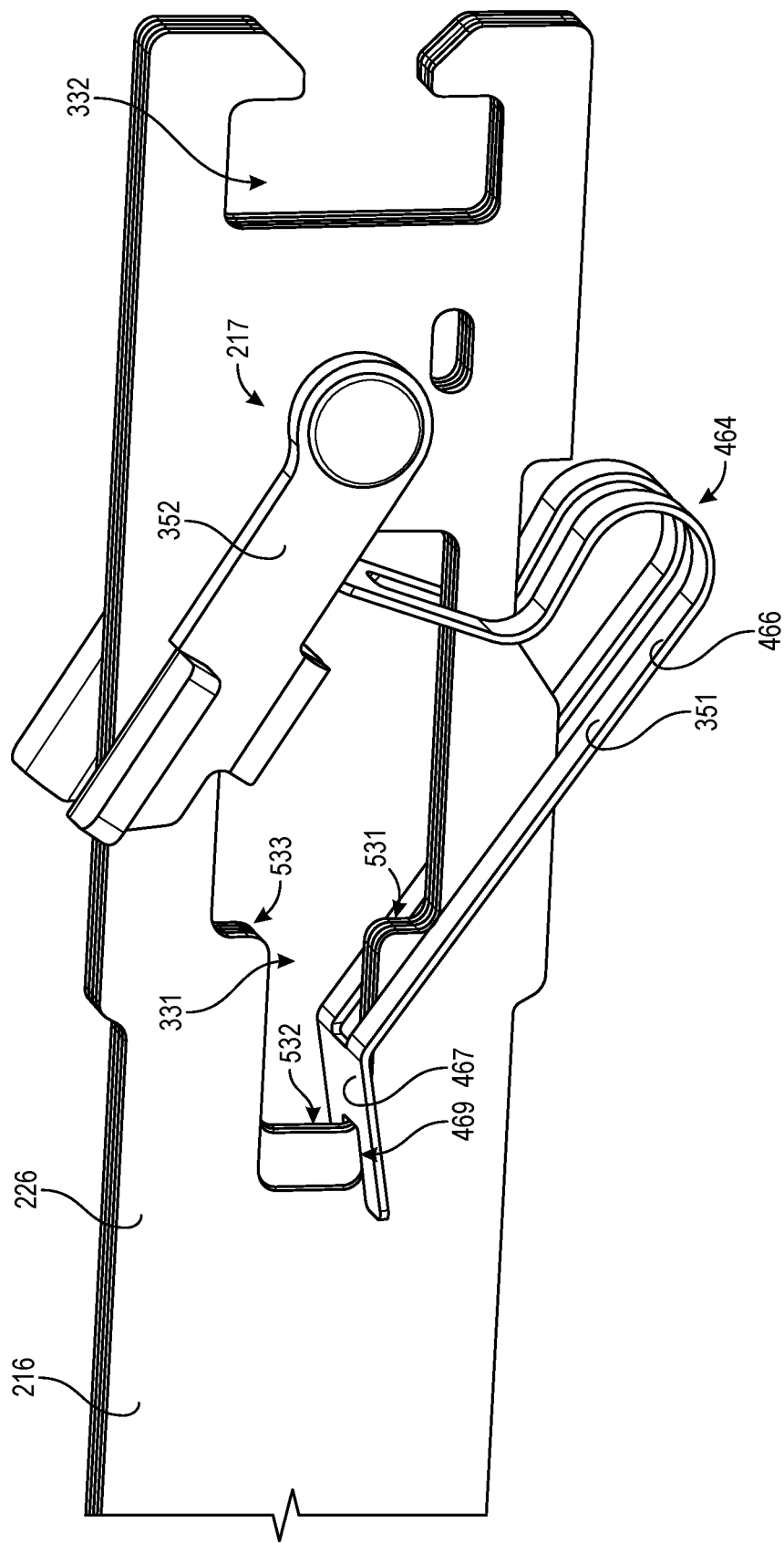
FIGS. 7A-7C are partially schematic side perspective views illustrating a self-correcting feature of a lockout assembly configured in accordance with various embodiments of the present technology.
Figure 7B:
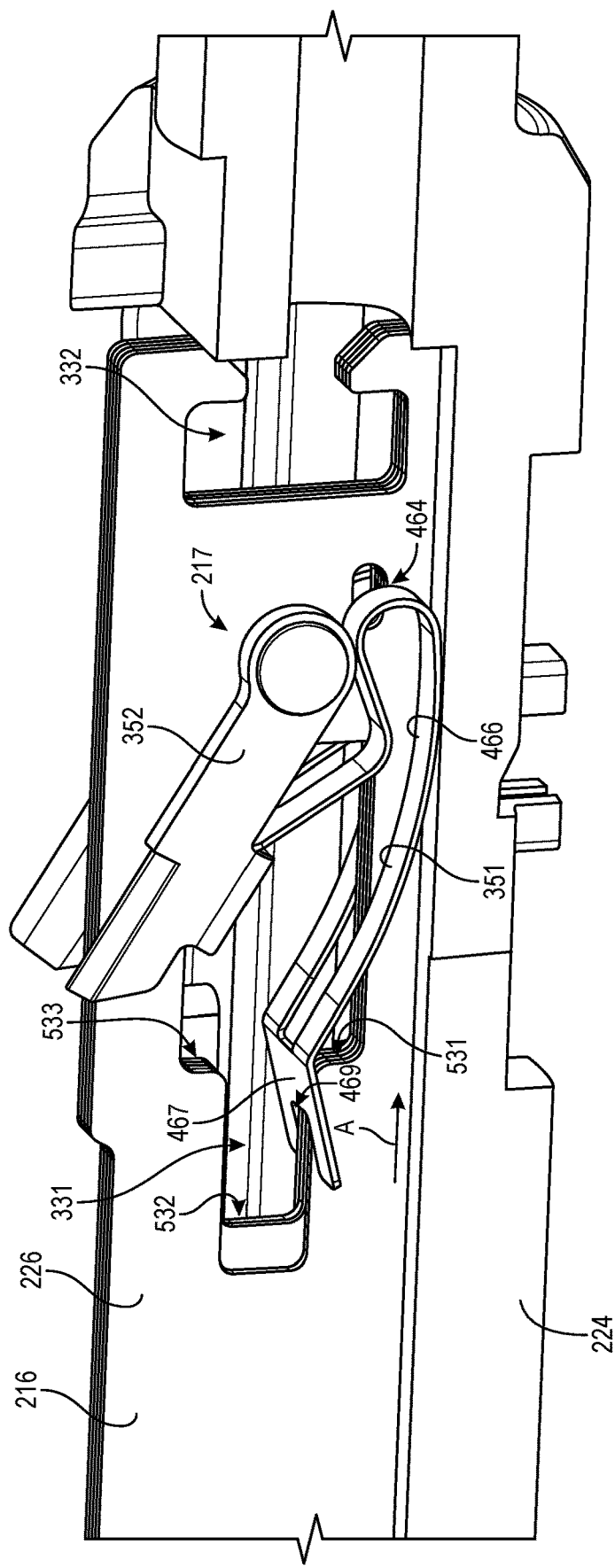
Figure 7C:
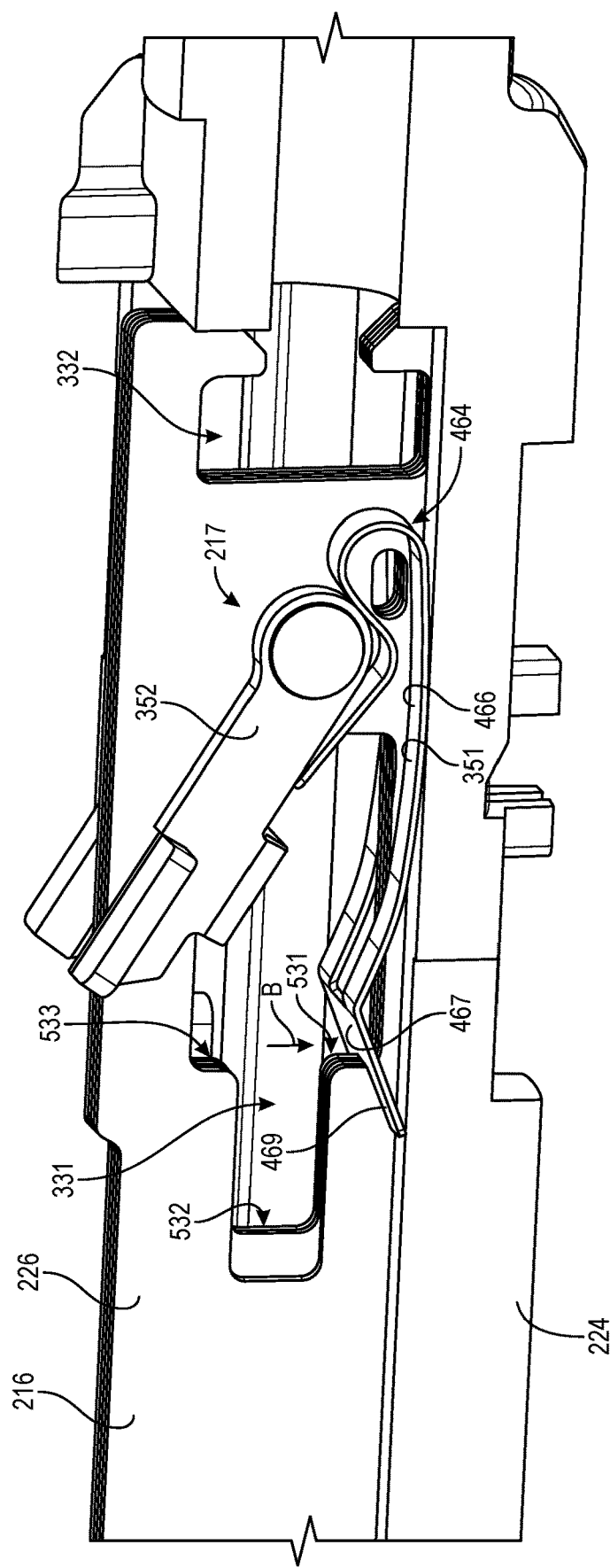

To address at least some of these improper installation scenarios, the spring 351 and/or the lockout assembly 217 can include various self-correcting features that can position or return the spring 351 to its properly installed state or position. For example, FIGS. 7A-7C are partially schematic side perspective views illustrating a self-correcting feature of the spring 351 and/or the lockout assembly 217. Referring first to FIG. 7A, the spring 351 of the lockout assembly 217 is shown improperly installed with the blade assembly 216. More specifically, the notch 469 of the spring 351 is resting against the second edge portions 532 of the first openings 331 of the leaves 226 (as opposed to the first edge portions 531 of the first openings 331) such that the fourth body portion 467 of the spring 351 straddles the second edge portions 532 (as opposed to the first edge portions 531). In this configuration, at least part of the third body portion 466 and/or at least part of the second body portion 464 of the spring 351 project a distance below the leaves 226 of the blade assembly 216. In some embodiments, this distance can be greater than a distance by which these same parts of the third body portion 466 and/or the second body portion 464 project beneath the leaves 226 when the spring 351 is properly installed.

Referring now to FIG. 7B, as the second cover portion 224 is installed with the blade assembly 216, the second cover portion 224 can engage portions of the third body portion 466 and/or the second body portion 464 of the spring 351 that project beneath the leaves 226 of the blade assembly 216. As the second cover portion 224 engages with the third body portion 466 and/or the second body portion 464 of the spring 351, the second cover portion 224 can apply a force against the third body portion 466 and/or second body portion 464 that moves these portions of the spring 351 generally upward (e.g., toward the mechanical latch 352) and/or generally to the right (e.g., generally toward the slots 332 in the leaves 226). In turn, the fourth body portion 467 of the spring 351 can be moved in a direction generally parallel to arrow A and toward the first edge portions 531 of the first openings 331.

Referring next to FIG. 7C, continued installation of the second cover portion 224 on the blade assembly 216 can continue to move the fourth body portion 467 of the first edge portions 531 generally parallel to the arrow A (FIG. 7B) until the top of the notch 469 clears the first edge portions 531. At this point, the fourth body portion 467 can move generally parallel to arrow B such that (a) the notch 469 rests against the first edge portions 531, (b) the fourth body portion 467 straddles the first edge portions 531, and (c) the first edge portions 531 are positioned or returned to their proper installation state or position. In some embodiments, a similar self-correcting feature of the spring 351 and/or the lockout assembly 217 can be employed to position or return the spring 351 to its proper installation state or position when the notch 469 is initially resting against the third edge portions 533 of the first openings 331 in the leaves 226 such that the fourth body portion 467 of the spring 351 straddles the third edge portions 533 instead of the first edge portions 531.

Figure 8:
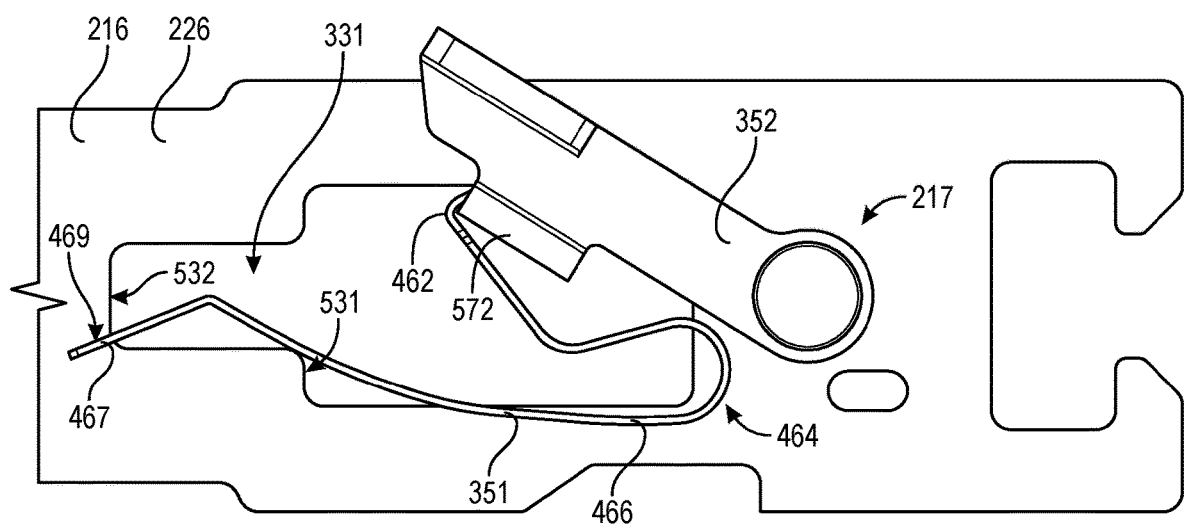
FIG. 8 is a partially schematic side view of a lockout assembly improperly installed with a blade assembly.

FIG. 8 illustrates another improper installation scenario for the lockout assembly 217. More specifically, FIG. 8 is a partially schematic side view of the spring 351 of the lockout assembly 217 improperly installed with the blade assembly 216. In particular, the notch 469 is resting against the second edge portions 532 of the first openings 331 in the leaves 226 of the blade assembly 216 such that the fourth body portion 467 of the spring 351 is straddling the second edge portions 532 (as opposed to the first edge portions 531). In addition, the hook portion 462 of the spring 351 is hooked on the bridge portion 572 of the mechanical latch 352 as opposed to being (i) positioned between the bridge portion 572 and the center body portion 576 (FIG. 5C) of the mechanical latch 352 and (ii) engaged with the center body portion 576. In this configuration, no part of the third body portion 466 or the second body portion 464 of the spring 351 projects a distance below the leaves 226 of the blade assembly 216. As such, it is unlikely that the second cover portion 224 (FIG. 2) will engage the third body portion 466 and/or the second body portion 464 when the second cover portion 224 is installed with the blade assembly 216. And even if the second cover portion 224 were to engage the third body portion 466 and/or the second body portion 464 during installation of the second cover portion 224, such engagement is unlikely to (a) unhook the hook portion 462 from the bridge portion 572 of the second edge portions 532, (b) position the hook portion 462 in the notch between the bridge portion 572 and the center body portion of the mechanical latch 352, and/or (c) properly engage the hook portion 462 with the center body portion 576. FIGS. 9A-10B described below illustrate embodiments of the present technology that address the improper installation scenario illustrated in FIG. 8.

Figure 9A:
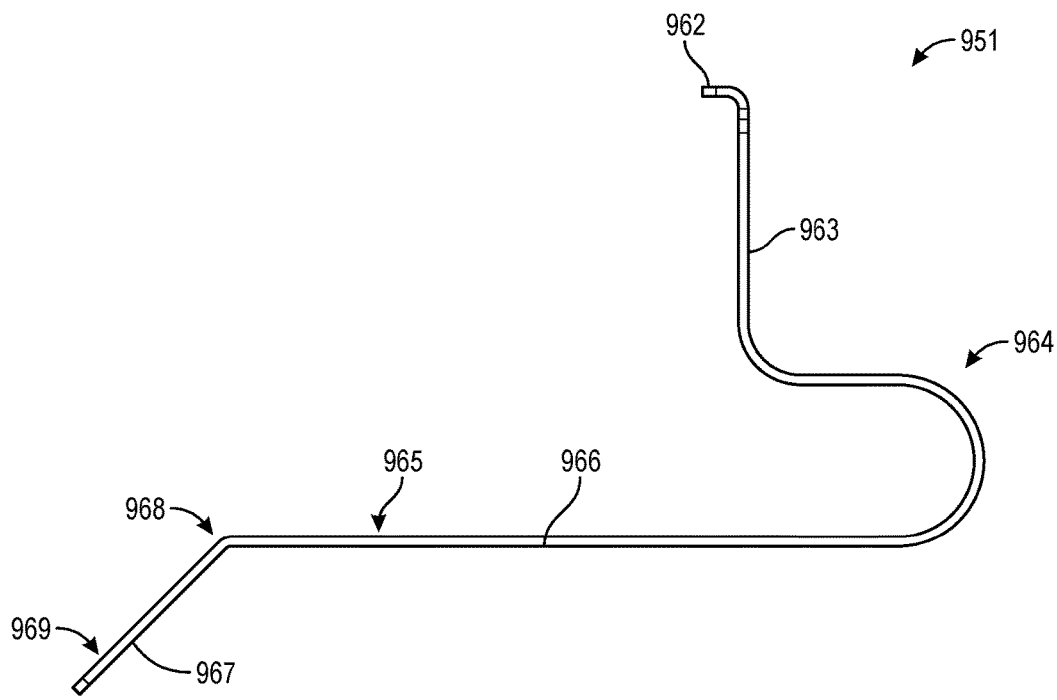
FIG. 9A is a partially schematic side view of another spring configured in accordance with various embodiments of the present technology.

FIG. 9A is a partially schematic side view of another spring 951 configured in accordance with various embodiments of the present technology. The spring 951 can be generally similar to the spring 351 described above with reference to FIGS. 3-8. Thus, similar reference numbers are used in FIG. 9A to denote identical or at least generally similar components. For example, the spring 951 includes a first body portion 963, a second body portion 964, a third body portion 966, a fourth body portion 967, and a bend 968 positioned between the third body portion 966 and the fourth body portion 967. The spring 951 further includes a cutout 965 at least generally similar to the cutout 465 of the spring 351, and a notch 969 at least generally similar to the notch 469 of the spring 351. The spring 951 additionally includes a hook portion 962 that is generally similar to the hook portion 462 of the spring 351 but that bends in a generally opposite direction from the direction of the bend of the hook portion 462.

Figure 9B:
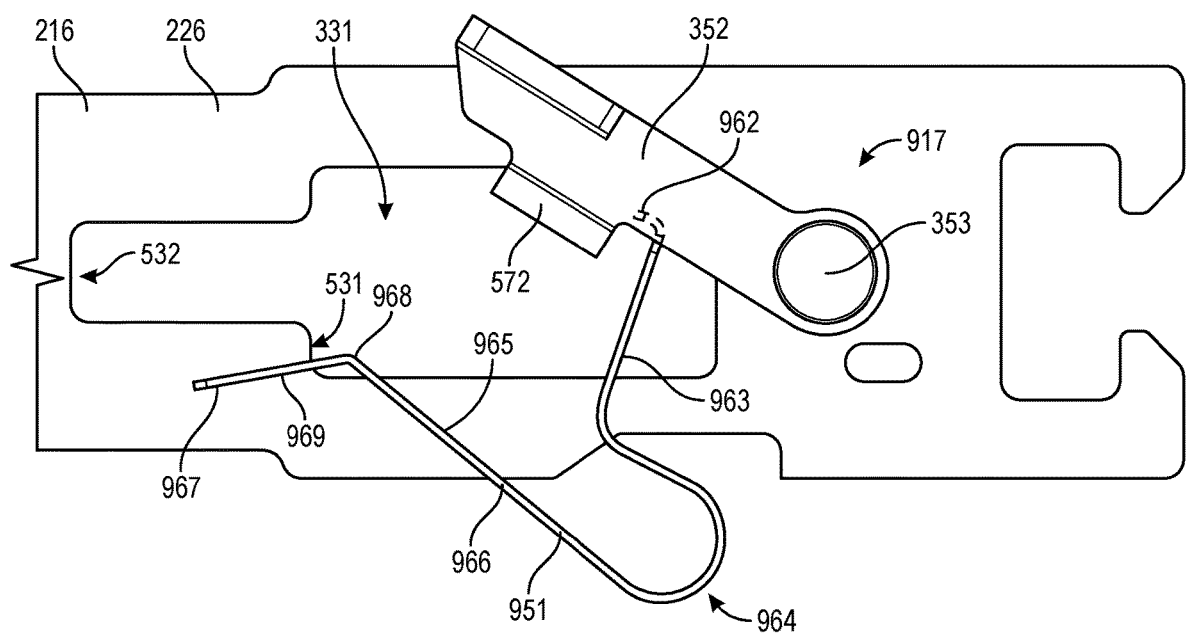
FIG. 9B is a partially schematic, partially transparent side view of another lockout assembly including the spring of FIG. 9A and configured in accordance with various embodiments of the present technology.

FIG. 9B is a partially schematic, partially transparent side view of a lockout assembly 917 including the spring 951 of FIG. 9A, and configured in accordance with various embodiments of the present technology. The lockout assembly 917 can be generally similar to the lockout assembly 217 described above with reference to FIGS. 3-8. Thus, similar reference numbers are used in FIG. 9B to denote identical or at least generally similar components. For example, the lockout assembly 917 can include the spring 951, the mechanical latch 352, and the pin 353. Additionally, or alternatively, the lockout assembly 917 can be installed with the blade assembly 216 in a manner generally similar to how the lockout assembly 217 can be installed with the blade assembly 216. For example, the mechanical latch 352 can be at least partially positioned within the first openings 331 in the leaves 226 and can be pivotably held in place at one end using the pin 353 that extends through the second openings 333 (FIG. 3) in the leaves 226. Furthermore, the spring 951 can be installed in the first openings 331 in such a manner that it engages the mechanical latch 352 and biases an unpinned end of the mechanical latch 352 in a generally upward direction (e.g., in a direction that extends generally toward a top of the leaves 226). More specifically, the spring 951 can be installed in the first openings 331 such that the notch 969 is resting against the first edge portions 531 of the first openings 331 and the fourth body portion 967 of the spring 351 straddles the first edge portions 531.

Due to the bend in the opposite direction from the direction of the bend in the hook portion 462 of the spring 351 discussed in detail above with reference to FIGS. 3-8, the hook portion 962 of the spring 951 in FIG. 9B can engage (hook) the center body portion 576 (FIG. 5C) at a side opposite the side at which the hook portion 462 the spring 351 engages the center body portion 576. In other embodiments, the hook portion 962 of the spring 951 can engage a proximal edge or portion of the bridge portion 572 of the mechanical latch 352. In any of these embodiments, the direction of the bend of the hook portion 962 prevents the hook portion 962 from engaging (hooking) the distal edge or portion of the bridge portion 572, thereby avoiding the improper installation scenario illustrated in FIG. 8.

Figure 10A:
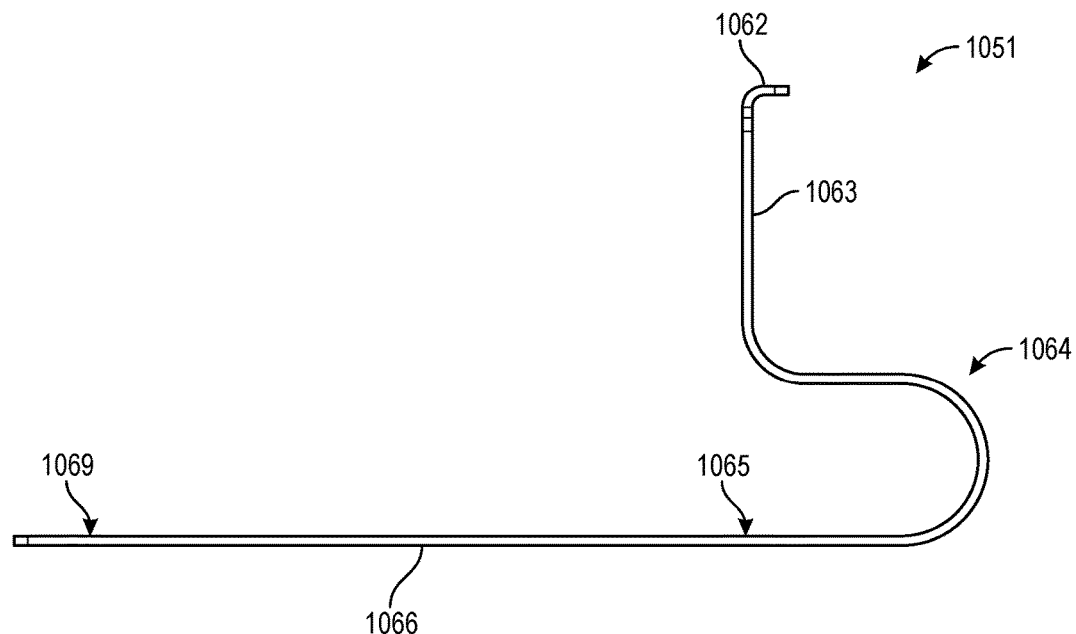
FIG. 10A is a partially schematic side view of another spring configured in accordance with various embodiments of the present technology.

FIG. 10A is a partially schematic side view of still another spring 1051 configured in accordance with various embodiments of the present technology. The spring 1051 can be generally similar to the spring 351 described above with reference to FIGS. 3-8 and/or the spring 951 described above with reference to FIGS. 9A and 9B. Thus, similar reference numbers are used in FIG. 10A to denote identical or at least generally similar components. For example, the spring 1051 includes a first body portion 1063, a second body portion 1064, and a third body portion 1066. The spring 1051 can further include a cutout 1065 at least generally similar to the cutout 465 of the spring 351 and/or to the cutout 965 of the spring 951, and a notch 1069 at least generally similar to the notch 469 of the spring 351 and/or to the notch 969 of the spring 951. The spring 1051 additionally includes a hook portion 1062 generally similar to the hook portion 462 of the spring 351 and/or to the hook portion 962 of the spring 951. The hook portion 1062 bends in a same general direction as the bend of the hook portion 462, and bends in a generally opposite direction from the direction of bend of the hook portion 962. Unlike the spring 351 and the spring 951, the spring 1051 does not include a bend and a fourth body portion similar to the bends 468 and 968 and fourth body portions 467 and 967, respectively, of the springs 351 and 951, respectively.

Figure 10B:
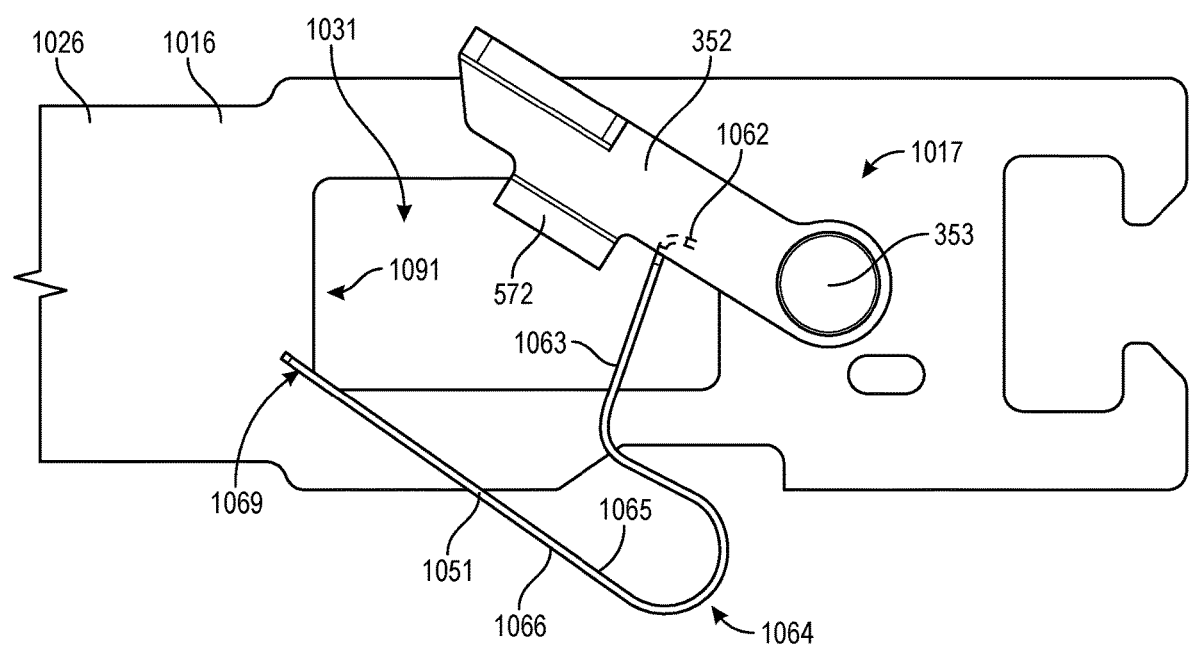
FIG. 10B is a partially schematic, partially transparent side view of still another lockout assembly including the spring of FIG. 10A and configured in accordance with various embodiments of the present technology.

FIG. 10B is a partially schematic, partially transparent side view of still another lockout assembly 1017 including the spring 1051 of FIG. 10A and configured in accordance with various embodiments of the present technology. The lockout assembly 1017 can be generally similar to the lockout assembly 217 described above with reference to FIGS. 3-8 and/or to the lockout assembly 917 described above with reference to FIG. 9B. Thus, similar reference numbers are used in FIG. 10B to denote identical or at least generally similar components. For example, the lockout assembly 1017 can include the spring 1051, the mechanical latch 352, and the pin 353. Additionally, or alternatively, the lockout assembly 1017 can be installed with a blade assembly 1016 in a manner generally similar to how the lockout assembly 217 and/or the lockout assembly 917 can be installed with the blade assembly 216 as described above. For example, the mechanical latch 352 can be at least partially positioned within first openings 1031 in leaves 1026 of the blade assembly 1016 and can be pivotably held in place at one end using the pin 353 that extends through second openings (not shown) in the leaves 1026 that are generally similar to the second openings 333 (FIG. 3) in the leaves 226 of the blade assembly 216. Furthermore, the spring 1051 can be installed in the first openings 331 in such a manner that it engages the mechanical latch 352 and biases an unpinned end of the mechanical latch 352 in a generally upward direction (e.g., in a direction that extends generally toward a top of the leaves 1026). More specifically, the hook portion 1062 of the spring 1051 can be (i) positioned in a notch between the bridge portion 572 of the mechanical latch 352 and the center body portion 576 (FIG. 5C) of the mechanical latch 352, and (ii) engaged with (hooked on) the center body portion 576.

In contrast with the first openings 331 in the leaves 226 of the blade assembly 216, the first openings 1031 in the leaves 1026 of the blade assembly 1016 includes fewer corners. More specifically, the first openings 1031 lack lips/edges similar to the first edge portions 531 and third edge portions 533 of the first openings 331 described above. Instead, the first openings 1031 are generally rectangular and each includes a single vertical edge 1091 at a distal portion of the first opening 1031. Thus, when the spring 1051 is installed with the blade assembly 1016, the notch 1069 rests against the edges 1091 of the first openings 1031 such that at least part of the third body portion 1066 of the spring 1051 straddles the edges 1091. Given (a) the size, shape, and geometric features of the spring 1051 and (b) the smaller width of the first openings 1031 in comparison to the first edge portions 531, the spring 1051 cannot be installed with (i) the hook portion 1062 engaged with the distal edge or portion of the bridge portion 572 of the mechanical latch 352 while (ii) the notch 1069 is resting against the edges 1091 such that at least part of the third body portion 1066 of the spring 1051 straddles the edges 1091. In other words, the spring 1051 and/or the blade assembly 1016 avoid the improper installation scenario illustrated in FIG. 8. Additionally, or alternatively, the spring 1051 and/or the lockout assembly 1017 can include self-correcting features that can position or return the spring 1051 to its proper installation state or position with the notch 1069 resting against a bottom portion of the edges 1091 (e.g., even when the notch 1069 is resting against an upper portion of the edges 1091 above the bottom portion).

Additional details regarding blade assemblies and/or lockout assemblies and, in particular, blade assemblies and/or lockout assemblies for surgical reloadable cartridge assemblies, are provided in U.S. patent application Ser. No. 17/669,683 and/or in U.S. patent application Ser. No. 18/391,251, the disclosures of which are both incorporated by reference herein in their entireties.

C. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order above, alternative embodiments may perform steps in a different order. Furthermore, the various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any material incorporated herein by reference conflicts with the present disclosure, the present disclosure controls.

Where the context permits, singular or plural terms may also include the plural or singular term, respectively. In addition, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded. Moreover, as used herein, the phrases "based on," "depends on," "as a result of," and "in response to" shall not be construed as a reference to a closed set of conditions. For example, an exemplary step that is described as "based on condition A" may be based on both condition A and condition B without departing from the scope of the present disclosure. In other words, as used herein, the phrase "based on" shall be construed in the same manner as the phrase "based at least in part on" or the phrase "based at least partially on."

From the foregoing, it will also be appreciated that various modifications may be made without deviating from the disclosure or the technology. For example, one of ordinary skill in the art will understand that various components of the technology can be further divided into subcomponents, or that various components and functions of the technology may be combined and integrated. In addition, certain aspects of the technology described in the context of particular embodiments may also be combined or eliminated in other embodiments. Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Furthermore, although several aspects of the present technology are discussed with reference to—and set forth in examples of the present technology directed to—systems, devices, and/or methods of the present technology, these aspects of the present technology can similarly be discussed with reference to—and be set forth in examples of the present technology directed to—any of systems, devices, methods, and/or (e.g., non-transitory) computer-readable media. As such, aspects of the present technology are not limited to the form (e.g., system, device, method, computer-readable medium) in which they are presented and described above.

We claim:

1. A lockout assembly for a surgical stapling apparatus, the lockout assembly comprising:
    a mechanical latch; and
    a spring configured to engage the mechanical latch, wherein:
        the spring includes a first end portion and a second end portion opposite the first end portion,
        the spring further includes (i) a hook portion at the first end portion and (ii) a loop portion, and
        in an absence of external force applied to the spring, the loop portion is generally positioned at a first side of the hook portion opposite the second end portion of the spring, and
    the spring is configured to engage the mechanical latch using the hook portion.

2. The lockout assembly of claim 1 wherein:
    the mechanical latch includes a proximal end portion, a distal end portion opposite the proximal end portion, a bridge portion positioned between the proximal end portion and the distal end portion, a center body portion positioned between the proximal end portion and the bridge portion, and a notch positioned between the bridge portion and the center body portion; and the hook portion is configured to be positioned in the notch and to engage a distal edge portion of the center body portion.

3. The lockout assembly of claim 1 wherein:

the mechanical latch includes a proximal end portion, a distal end portion opposite the proximal end portion, a bridge portion positioned between the proximal end portion and the distal end portion, a center body portion positioned between the proximal end portion and the bridge portion, and a notch positioned between the bridge portion and the center body portion; and the hook portion is configured (a) to be positioned in the notch and to engage a proximal edge portion of the bridge portion, or (b) to engage a proximal edge portion of the center body portion.

4. The lockout assembly of claim 1 wherein the spring includes a cutout extending at least partway between the hook portion and the second end portion of the spring.

5. The lockout assembly of claim 1 wherein the spring includes a notch at the second end portion of the spring.

6. The lockout assembly of claim 1 wherein the spring is a leaf spring.

7. A spring for a surgical stapler, the spring comprising:

a hook portion at a first end portion of the spring opposite a second end portion of the spring; and a loop portion that, in an absence of external force applied to the spring, is generally positioned at a first side of the hook portion opposite the second end portion such that the hook portion is positioned generally along a plane positioned between the loop portion and the second end portion.

8. The spring of claim 7 wherein the spring is a leaf spring.

9. The spring of claim 7 wherein, in the absence of the external force applied to the spring, the loop portion has a bend that is concave in a direction generally toward the plane.

10. The spring of claim 7, further comprising a cutout extending at least partway between the hook portion and the second end portion.

11. The spring of claim 10 wherein the cutout extends along an entire length of the loop portion.

12. The spring of claim 7 wherein the hook portion has a bend that is concave in a direction generally away from the second end portion of the spring.

13. The spring of claim 7 wherein the hook portion has a bend that is concave in a direction generally toward the second end portion of the spring.

14. The spring of claim 7, further comprising:

a body portion at the second end portion of the spring;

a notch formed in the body portion; and a bend positioned between the body portion and the loop portion such that the body portion slants in a direction generally downward and away from the loop portion, starting from the bend.

15. The spring of claim 7, further comprising:

a first body portion extending at least partway between the hook portion and the loop portion, and oriented in a first orientation generally parallel to the plane; and a second portion extending at least partway between the loop portion to the second end portion of the spring, and oriented in a second orientation that is generally perpendicular to the first orientation.

16. The spring of claim 7 wherein the spring is generally 'S' shaped.

17. The spring of claim 7 wherein the spring is formed at least in part by stainless steel.

18. A reloadable cartridge assembly, comprising:

a blade assembly including a leaf and an I-beam at a distal end portion of the leaf, wherein the leaf includes a first opening and a second opening; and a lockout assembly including a spring, a mechanical latch having a first end portion and a second end portion opposite the first end portion, and a pin, wherein the lockout assembly is configured to be installed with the blade assembly such that (a) the mechanical latch is at least partially positioned within the first opening, (b) the pin is at least partially positioned in the second opening and pivotably retains the first end portion of the mechanical latch in place, and (c) the spring is at least partially positioned in the first opening and is engaged with the mechanical latch such that the spring biases the second end portion of the mechanical latch in a first general direction, wherein— the spring includes a first end portion and a second end portion opposite the first end portion, the spring further includes (i) a hook portion at the first end portion of the spring and (ii) a loop portion, in an absence of external force applied to the spring, the loop portion is generally positioned at a first side of the hook portion opposite the second end portion of the spring, and when the lockout assembly is installed with the blade assembly, the spring engages the mechanical latch using the hook portion.

19. The reloadable cartridge assembly of claim 18 wherein:

the spring includes a notch at the second end portion of the spring;

when the lockout assembly is installed with the blade assembly, the notch abuts against an edge of the first opening;

the spring further includes a cutout extending at least partway between the hook portion and the notch; and when the lockout assembly is installed with the blade assembly, at least a portion of the leaf is positioned within the cutout such that at least a portion of the spring straddles the leaf.

20. The reloadable cartridge assembly of claim 18 wherein:

the reloadable cartridge assembly further comprises a cover portion configured to be installed with the blade assembly;

when the lockout assembly is installed with the blade assembly without the cover portion installed with the blade assembly, at least a portion of the spring projects beyond an outer profile of the leaf; and when the cover portion and the lockout assembly are installed with the blade assembly, the cover portion exerts a force on at least the portion of the spring.

* * * * *